US008624727B2

(12) United States Patent
Saigh et al.

(10) Patent No.: US 8,624,727 B2
(45) Date of Patent: Jan. 7, 2014

(54) PERSONAL SAFETY MOBILE NOTIFICATION SYSTEM

(75) Inventors: Michael Martin Saigh, Clayton, MO (US); Kevin Richard Arndt, Summit Hill, PA (US); Andrew Victor Saigh, St. Louis, MO (US)

(73) Assignee: Saigh and Son, LLC, St. Louis, MO (US)

( * ) Notice: Subject to any disclaimer, the term of this patent is extended or adjusted under 35 U.S.C. 154(b) by 0 days.

(21) Appl. No.: 13/554,692

(22) Filed: Jul. 20, 2012

(65) Prior Publication Data

US 2013/0183924 A1 Jul. 18, 2013

Related U.S. Application Data

(63) Continuation-in-part of application No. 12/011,577, filed on Jan. 28, 2008, now Pat. No. 8,013,734, and a continuation-in-part of application No. 13/022,066, filed on Feb. 7, 2011.

(60) Provisional application No. 61/509,757, filed on Jul. 20, 2011.

(51) Int. Cl.
*G08B 1/08* (2006.01)

(52) U.S. Cl.
USPC .............. 340/539.13; 340/539.1; 340/539.11; 340/541; 340/573.1; 340/825.49; 455/404.1; 455/521

(58) Field of Classification Search
USPC ............... 340/539.13, 539.1, 539.11, 539.23, 340/541, 573.1, 825.49, 825.69; 455/404.1, 455/521, 456, 456.1, 456.2, 456.3
See application file for complete search history.

(56) References Cited

U.S. PATENT DOCUMENTS

| 5,929,777 | A | 7/1999 | Reynolds |
| 6,044,257 | A | 3/2000 | Boling et al. |
| 7,233,781 | B2 | 6/2007 | Hunter et al. |
| 7,251,471 | B2 | 7/2007 | Boling et al. |
| 7,259,694 | B2 | 8/2007 | Myllymaki et al. |
| 7,308,246 | B2 | 12/2007 | Yamazaki et al. |
| 7,315,735 | B2 * | 1/2008 | Graham ..................... 455/404.1 |
| 7,355,507 | B2 | 4/2008 | Binning |
| 7,409,428 | B1 | 8/2008 | Brabec et al. |
| 7,411,493 | B2 * | 8/2008 | Smith ....................... 340/539.18 |
| 8,219,110 | B1 * | 7/2012 | White et al. ................ 455/456.1 |
| 2003/0050039 | A1 * | 3/2003 | Baba et al. ................... 455/404 |
| 2007/0072581 | A1 * | 3/2007 | Aerrabotu .................. 455/404.1 |
| 2007/0182548 | A1 | 8/2007 | Raad |
| 2008/0070546 | A1 * | 3/2008 | Lee ............................ 455/404.2 |

* cited by examiner

*Primary Examiner* — Hung T. Nguyen

(57) ABSTRACT

In described embodiments, a system establishes a perimeter around an area, and mobile devices within the established perimeter communicate with a server that provides and collects personal and asset safety information. The provided information might enable users associated with the mobile devices to plan actions or take routes based on a given criteria, such as a safest route, through display on the mobile device. The collected information from the mobile device might be location, emergency event, environmental factors, sensor information and the like, which might then be communicated to users and/or administrators of the system. Location information, such as through global positioning system (GPS), might provide tracking of mobile devices and users or assets associated with each mobile device. GPS functionality associates latitude, longitude and elevation (X-Y-Z coordinate axis) data with the collected and provided information.

20 Claims, 23 Drawing Sheets

300

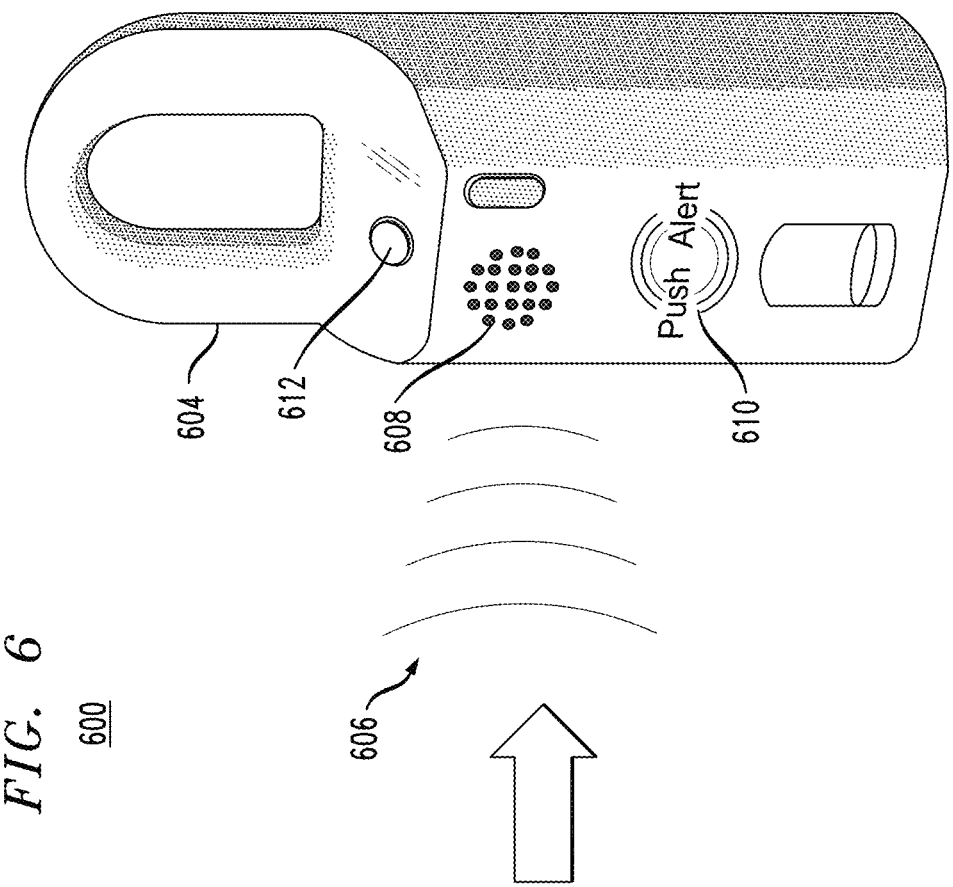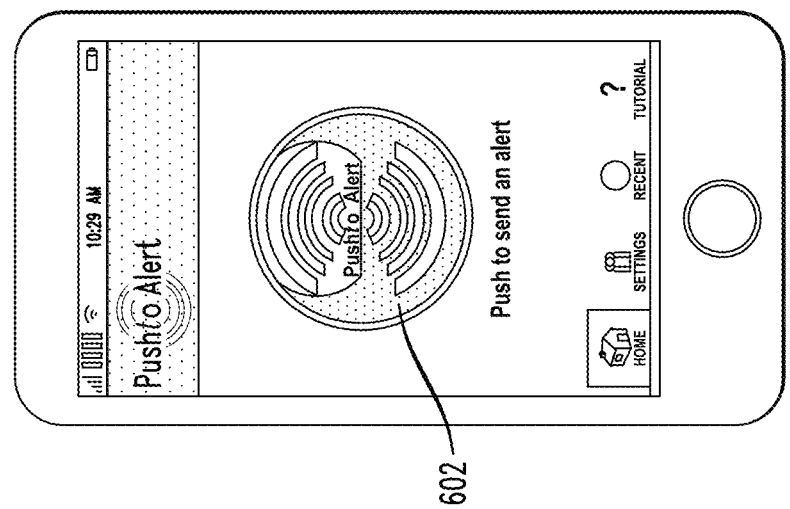

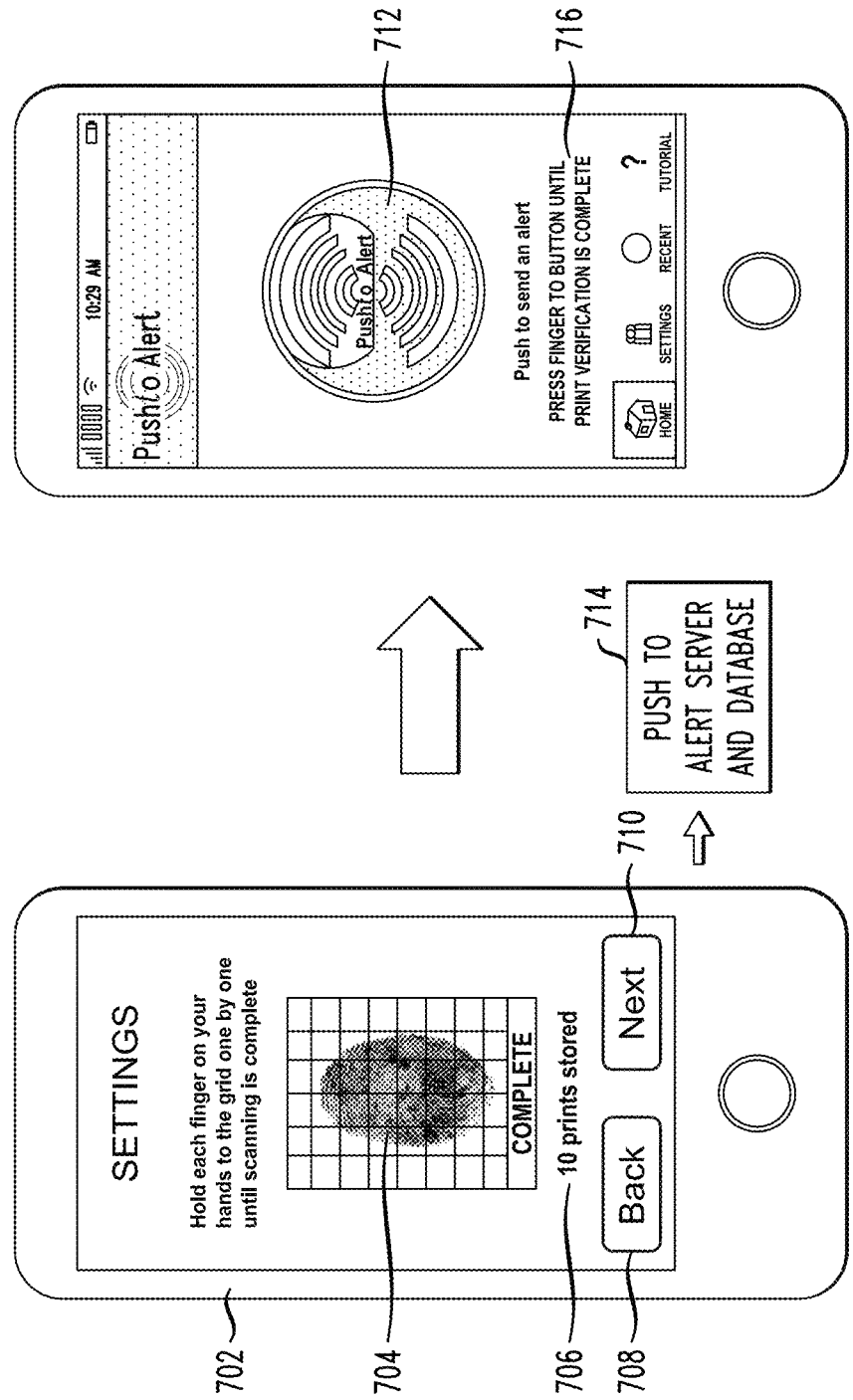

800

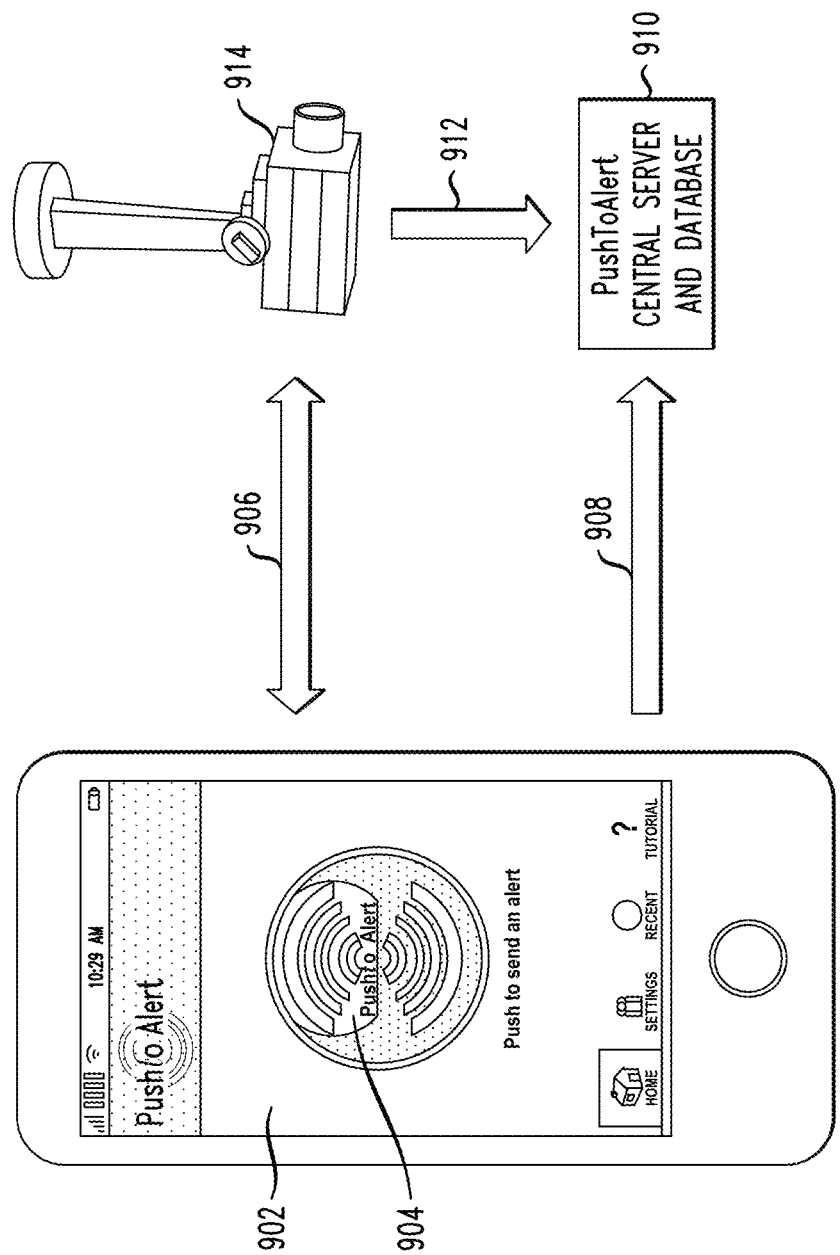

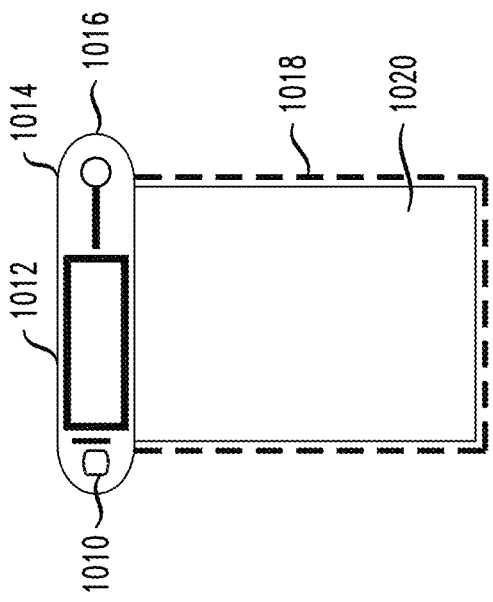
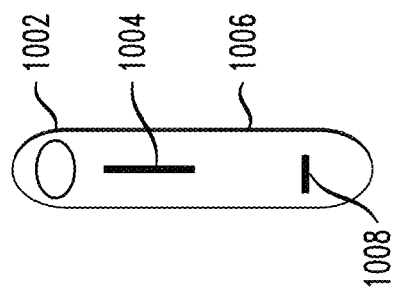

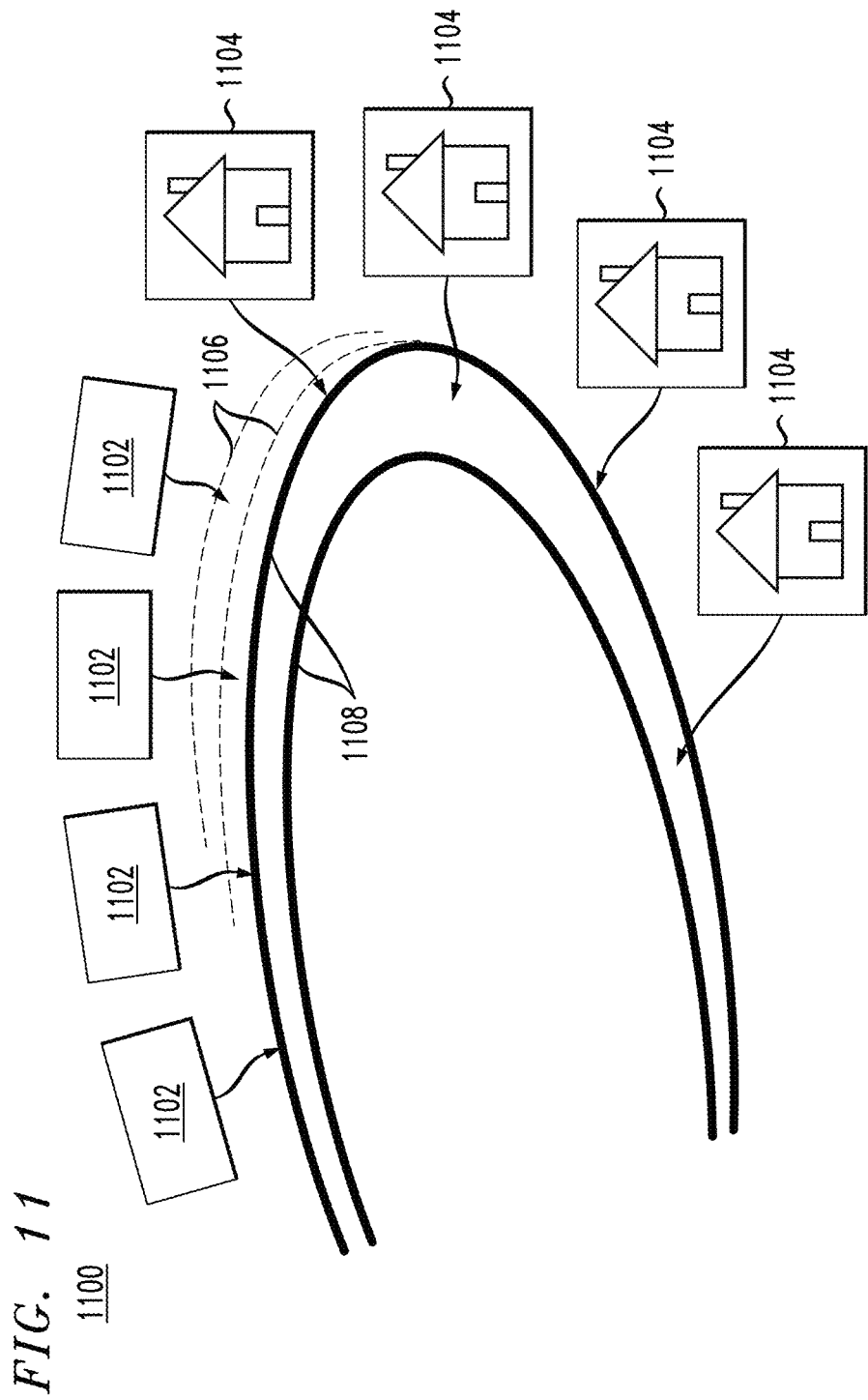

MOBILE ASSET MGT SYSTEM
*ASSET SENSOR ALERTS*

| ENV. SENSORS | RFID ALERT DATA | ENV. SENSORS | RFID ALERT DATA |
|---|---|---|---|
| TEMPERATURE ALERTS – 6 | RFID #'s | VIBRATION ALERT – 5 | RFID #'s |
| LIGHT EXPOSURE ALERTS – 43 | RFID #'s | WEATHER ALERTS – 77 | RFID #'s |
| SMOKE ALERTS – 12 | RFID #'s | CHEMICAL ALERTS – 2 | RFID #'s |
| HUMIDITY ALERTS – 405 | RFID #'s | WATER ALERTS – 16 | RFID #'s |
| AIR COMPOSITION ALERTS – 15 | RFID #'s | GIS ALERTS DATA | RFID #'s |
| TRANSIT TRACK ALERTS 8 LOCATOR | | THEFT ALERT | PROXIMITY ALERT |

- 1503 — ENV. SENSORS
- 1504 — RFID ALERT DATA
- 1501 — TEMPERATURE ALERTS
- 1506 — GIS ALERTS DATA
- 1502(a.) — TRANSIT TRACK ALERTS 8
- 1502(b.) — LOCATOR
- 1507 — THEFT ALERT
- 1505 — PROXIMITY ALERT

<<NEXT>>

PERSONAL SAFETY MOBILE NOTIFICATION SYSTEM

CROSS-REFERENCE TO RELATED APPLICATIONS

This application is a continuation-in-part, and claims the benefit of the filing date, of U.S. patent application Ser. Nos. 12/011,577 filed Jan. 28, 2008, now U.S. Pat. No. 8,013,734 and 13/022,066 filed Feb. 7, 2011, the teachings of which are incorporated herein in their entireties by reference. This application claims the benefit of the filing date of U.S. provisional application No. 61/509,757, filed on Jul. 20, 2011.

BACKGROUND OF THE INVENTION

1. Field of the Invention

The present invention relates to an emergency notification system and, specifically, a personal safety mobile notification system with geographic tracking capability.

2. Description of the Related Art

A typical cellular or mobile phone system divides a geographic area into one or more "cells" with corresponding cellular towers. User devices (wireless mobile phones, computers, security systems, etc.) that are in a cell are in communication with one or more of the cellular towers responsible for the cell. Each cellular tower typically has a corresponding base station containing a power source and communication equipment in communication with a main communication system of the cellular phone system through a Mobile Switching Office (MTSO) or Mobile Switching Center (MSC). The phrase "public land mobile network (PLMN)" will be used to represent the entire mobile device communication network, regardless of the type of technology used in the communication network (e.g., GSM, PCS, CDMA, UMTS, etc). The PLMN might typically control any base station with which it is in communication, and might handle connections from cellular tower to cellular tower and from a cellular tower to the normal land-based phone system. While the term "cell" or "cellular" is used herein to refer to certain type of mobile device communication protocols, this term is used in its broadest sense to include other communications systems such as personal communications service ("PCS") protocol, and the Global System for Mobile communications ("GSM") protocol, or other similar communications protocols.

A cellular phone switches cells, and, thus, towers, as the phone is moved between geographic areas, allowing constant communication with the PLMN. Typically, a cellular phone has one or more codes associated with it, used to identify the specific phone, the phone's owner and the phone's service provider. For example, a cellular phone might have an Electronic Serial Number (ESN) or Mobile Equipment IDentifier (MEID) that is programmed into the phone when it is manufactured, a Mobile Identification Number (MIN) that is derived from the phone's number, and a System Identification Code (SID) that is assigned to each carrier by the Federal Communication Commissioner (FCC). While the ESN or MEID are considered a permanent part of the phone, both the MIN and SID codes are programmed into the phone when the cell phone is activated by a carrier. Additionally, many cellular phones include a Subscriber Identity Module (SIM) memory card. A SIM card is a removable card that stores a service-subscriber key (IMSI) used by a carrier to identify a subscriber.

When a cell phone is first activated, it transmits a signal seeking the nearest cellular tower/base station, for example, to transmit a registration request, so that the PLMN can track the cell phone's approximate geographic location in a database. Even when the cell phone is not activated, the cell phone is in communication with the tower/base station over one or more control channels. In this regard, the PLMN can obtain approximately real-time data representing the approximate location of the cell phone. The PLMN's tracking of the cell phone's geographic location is used mainly to compute which cell phone tower is nearest the cell phone as the cell phone moves, so as to allow for more efficient communication switching when the phone is mobile. Thus, for example, when the PLMN receives an incoming communication for a particular cell phone, the PLMN locates the particular cell phone in its database, locates the nearest cellular tower, and forwards the incoming communication to the nearest cellular tower to complete the communication path. Many cell phones also employ the control channel(s) for the transmission of Short Message Service (SMS) messages between a source cell phone and the tower/base station. Once an SMS message is created and sent from the cell phone, the message is sent to the PLMN, which then routes the message to the cellular telephone network through an SMS gateway. The message travels to a short message service center (SMSC), which then transmits the message to the cell phone tower nearest to a destination cell phone, and the tower then relays the message to the destination cell phone.

Current mobile technology schemes for warning the general public of an emergency situation, for example a terrorist act, crime, fire, natural disaster, or any other category of potentially or actually harmful event have numerous inherent disadvantages. For example, broadcast messaging (like SMS messaging), are a passive technology that do not allow subscribers to actively interact, interface, trigger or activate a location's alarm or siren network within a proximity of the emergency. Additionally, current mobile technology schemes do not allow for "real time" forensic information to be electronically collected, stored or transferred to emergency personnel and/or other organizations in order to help prevent further injury or to gather information about the emergency.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention allows for a personal safety notification system including a plurality of mobile devices in wireless communication with a network. A server, coupled to the network, communicates with each mobile device, wherein the server is coupled to a database comprising personal safety information related to predefined alerts/events, and is coupled to one or more other databases including one or more of geographic, topological, building, structure and area configuration information. A plurality of nodes provides a perimeter about an area and are coupled to the server wherein, when one or more of the plurality of mobile devices enters the area, the corresponding mobile device enters an active sub-network within the personal safety notification system coordinated by the server. The server further receives alert/event details from each mobile device in the active sub-network, and provides the alert/event details to specific ones of the plurality of mobile devices in the active sub-network in response to the occurrence of a given alert/event, the alert/event details including X-Y-Z coordinate information for aspects of the area within the active sub-network.

In another embodiment, the present invention allows for a mobile device coupled to a server providing database information related to a personal safety notification system. The mobile device includes a sensor that reads alert/event data in proximity to the mobile device, a processor that controls collection of the alert/event data by the sensor of the mobile device, the alert/event data having associated X-Y-Z coordinate information of the mobile device and each alert/event; a memory that stores the alert/event data collected by the mobile device, and a wireless transceiver, in wireless communication with the server, that transfers the alert/event data collected by the mobile device to the server. When the mobile device enters an area defined by a plurality of nodes configured to provide a perimeter about the area and coupled to the server, the mobile device enters an active sub-network within a personal safety notification system coordinated by the server through communication with the processor through the wireless transceiver.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 6 shows an exemplary specialized alert configuration for a real estate key lock box, in accordance with embodiments of the present invention;

FIG. 7 shows an exemplary fingerprint alert application, in accordance with embodiments of the present invention;

FIG. 9 shows a block diagram of a mobile device enabling a peripheral video surveillance camera, in accordance with embodiments of the present invention;

FIGS. 10A-10C show block diagrams of exemplary hidden cameras which can encapsulate data of the alert hotspot emergency, in accordance with embodiments of the present invention;

FIG. 11 shows a real-time emergency database providing X-Y coordinates of various emergencies in conjunction with the mobile whereabouts of the smartphone, in accordance with embodiments of the present invention;

FIG. 15 shows an exemplary smartphone equipped with a reader screen display exemplifying various real-time and archival sensor data from one or more RFID sensor devices;

DETAILED DESCRIPTION

Table 1 defines a list of acronyms employed throughout this specification as an aid to understanding the described embodiments of the present invention:

TABLE 1

| | | | |
|---|---|---|---|
| MTSO | Mobile Telephone Switching Office | MSC | Mobile Switching Center |
| PLMN | Public Land Mobile Network | UMTS | Universal Mobile Telecommunications System |
| GSM | Global System for Mobile Communications | PCS | Personal Communications Service |
| CDMA | Code Division Multiple Access | WCDMA | Wideband Code Division Multiple Access |
| TDMA | Time Division Multiple Access | GPS | Global Positioning System |
| SMS | Short Message Service | SMSC | Short Message Service Center |
| PSTN | Public Switched Telephone Network | DNS | Domain Name Server |
| IP | Internet Protocol | GMLC | Gateway Mobile Location Center |
| SIM | Subscriber Identification Module | SID | System Identification Code |
| MIN | Mobile Identification Number | ESN | Electronic Serial Number |
| MEID | Mobile Equipment IDentifier | IMSI | International Mobile Subscriber |

TABLE 1-continued

| | | | |
|---|---|---|---|
| | | | Identity |
| CVR | Cockpit Voice Recorder | FDR | Flight Data Recorder |
| USB | Universal Serial Bus | SD | Secure Digital |
| PDA | Personal Digital Assistant | DSP | Digital Signal Processor |
| CBMD | Cellular Based Motion Detector | PI | Push Initiator |
| MSM | Mobile Safety Management Software Program | CAD | computer-aided dispatch |

Figure 1:
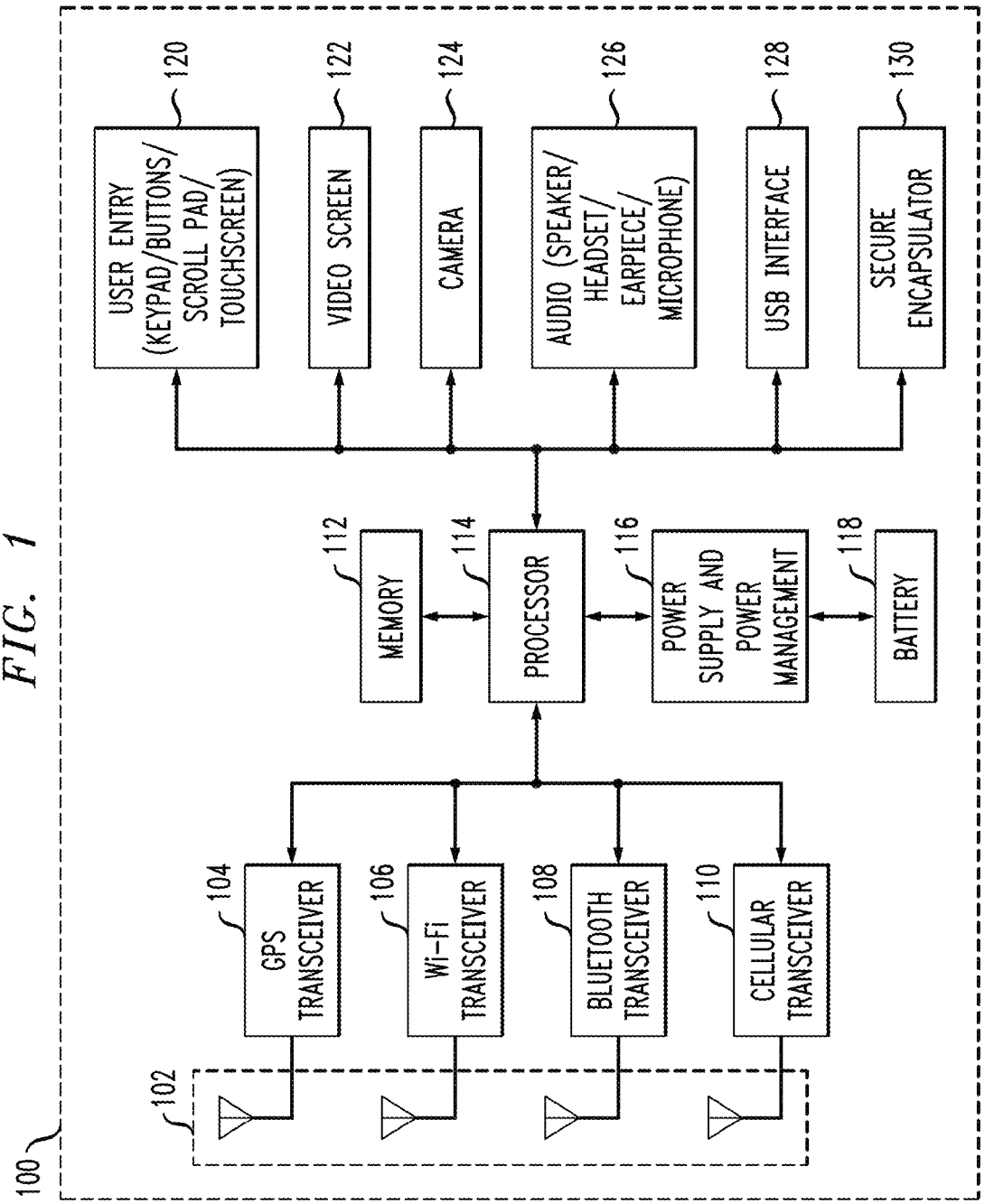
FIG. 1 shows a block diagram of a mobile device having a secure encapsulator, in accordance with embodiments of the present invention.

FIG. 1 shows a block diagram of mobile device 100 including, secure encapsulator 130. Mobile device 100 might be a cellular telephone, PDA, or other mobile communications device. As shown, mobile device 100 includes GPS transceiver 104 for communication with the satellite-based global positioning system, and wi-fi transceiver 106 for communication with a wireless network, for example, a wireless network operating in accordance with one or more of the 802.11 communication standards. Mobile device 100 includes Bluetooth® transceiver 108 for communication with wireless peripheral devices, for example, devices operating in accordance with the 802.15 communication standard. Cellular transceiver 110 is for communication with Public Land Mobile Network (PLMN), for example, in accordance with one or more mobile communications standards such as UMTS, PCS, GSM, 3G, 4G, or others. As indicated by the dashed line, one or more of transceivers 104, 106, 108 and 110 might share one or more common antennas 102.

Mobile device 100 might include one or more microcontrollers or digital signal processors (DSPs), shown collectively in FIG. 1 as processor 114. Processor 114 might typically include at least a portion of an operating system of mobile device 100, perform signal processing for signals received from or transmitted to transceivers 104, 106, 108 and 110, and generally control operation of other modules of mobile device 100. Processor 114 interfaces with memory 112, which might include one or more memories for storage of for example, the operating system of mobile device 100, software applications installed on mobile device 100, various user data such as contact information, calendar information, text messages, email messages, photographs, videos, or other electronic files. Memory 112 might be internal to the hardware of mobile device 100, might be on a memory card, such as a micro Secure Digital (SD) card, inserted into mobile device 100, or some combination thereof.

Mobile device 100 is powered by battery 118 via power supply and power manager 116, which might typically provide required operating voltages of mobile device 100 and manage recharging of battery 118. User entry 120, which might include a touch screen input, keypad, buttons, scroll wheel, touch pad, voice commands, or other input to mobile device 100. Mobile device 100 displays output data on video screen 122, and provides output audio data to and receives audio input data from audio input and output 126. Mobile device 100 might typically include camera 124 for taking still photos and/or videos. Universal Serial Bus (USB) interface 128 might allow mobile device 100 to be plugged in to various USB devices, such as a computer. Mobile device 100 might operate substantially as described in parent U.S. patent application Ser. No. 12/011,577 filed Jan. 28, 2008. In accordance with embodiments of the present invention, mobile device 100 also includes secure encapsulator 130.

As described in parent U.S. patent application Ser. No. 13/022,066 filed Feb. 7, 2011, secure encapsulator 130 might, when activated, record at least some portion or all of sensor based data of mobile device 100. The sensor data might be sourced in any format, protocol and technology including, but not limited to, audio, video, thermal imaging, still images, biological data, GPS location data, cellular tower data, and the like. Secure encapsulator 130, when activated, might store such data leading up to, and during, the activation of an emergency alert mode of mobile device 100. Alternatively, secure encapsulator 130 might collect sensor data over a predefined period, where when the period is reached newer data overwrites older data. In addition, secure encapsulator 130 might activate additional sensors, either local to mobile device 100, or remote to mobile device 100 through one or more of transceivers 104, 106, 108 and 110, to help record data pertaining to the emergency alert and enhance any sensors available on mobile device 100. Secure encapsulator 130 might typically, in order to save memory space, store data for a determined period of time, before erasing or overwriting the stored data. Thus, secure encapsulator 130 might be configured with programmed time duration to track, or programmed time duration to maintain the tracked data.

Figure 2:
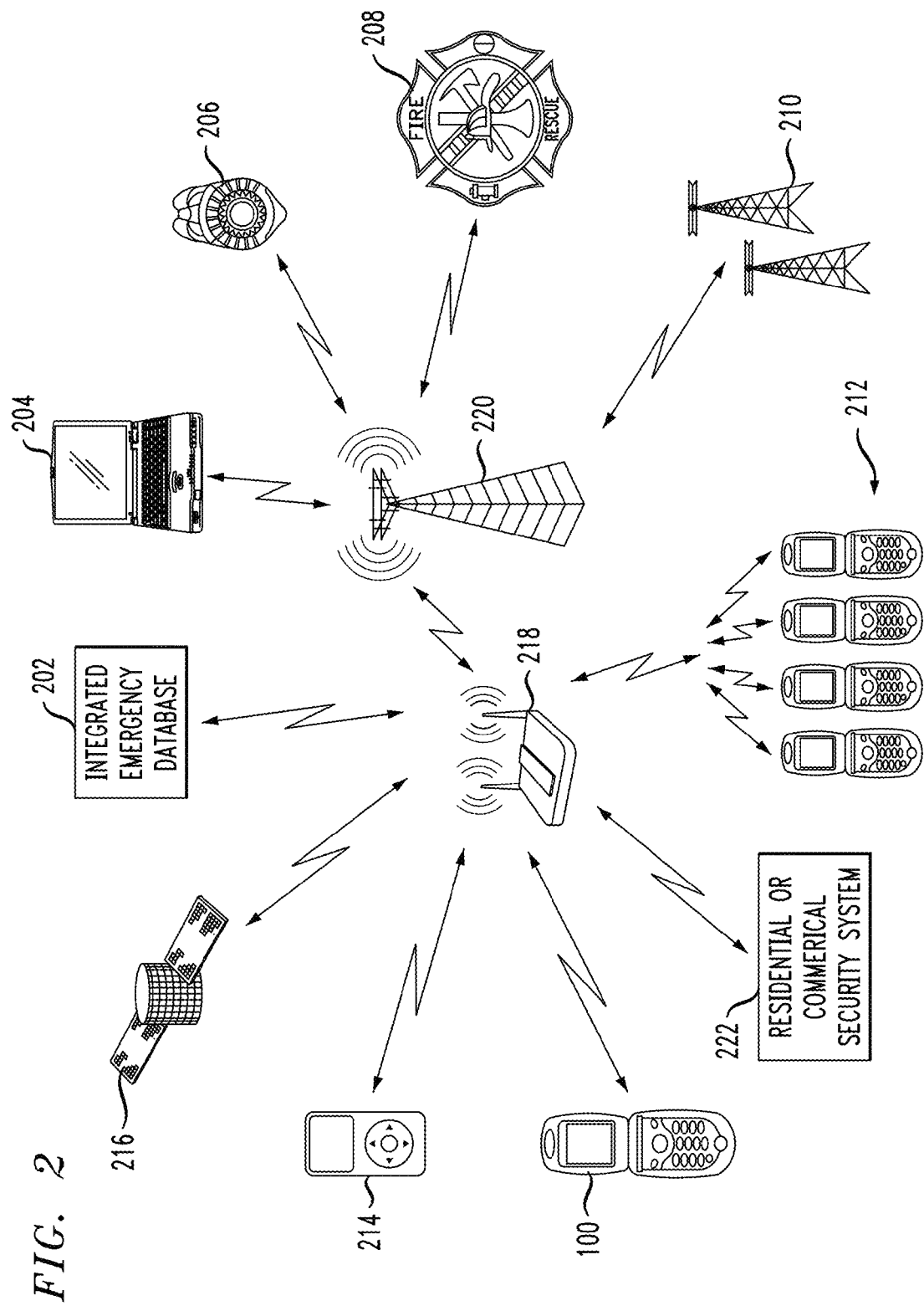
FIG. 2 shows a logical diagram of a system employing one or more of the mobile devices of FIG. 1 and an integrated emergency database, in accordance with embodiments of the present invention.

FIG. 2 shows a logical diagram of communications by mobile device 100 that might be initiated and managed by secure encapsulator 130. As shown in FIG. 2, secure encapsulator 130 might cause mobile device 100 to transfer recorded data via at least one of transceivers 104, 106, 108 and 110, to integrated emergency database 202, for example, via cellular tower 220 or wi-fi router 218. Integrated emergency database 202 might then initiate communication to one or more of law enforcement services 206, emergency services 208, one or more remote computers 204, and one or more other mobile devices 212 and portable electronics 214. The other mobile devices 212 might be within a given proximity of mobile device 100. Thus, mobile device 100 might transmit an electronic emergency alert signal if the user of mobile device 100 encounters an emergency situation or becomes incapacitated. Secure encapsulator 130 might enable tracking of the location of mobile device 100 through GPS system 216, such that other mobile devices in proximity to the alert might be notified of the emergency situation. Further, GPS system 216 might be employed to provide the user of mobile device 100, or mobile devices 212 in proximity to mobile device 100 based on the integrated emergency database, with information to escape from the emergency situation. Integrated emergency database 202 might track individuals, police units, members of a given class (e.g., corporate employees, students, family members, etc.).

Integrated emergency database 202 might generally operate such as described in parent U.S. patent application Ser. No. 13/022,066 filed Feb. 7, 2011 to gather data on an emergency or crime as it occurs. For example, integrated emergency database 202 might gather information about the location and conditions of the emergency or crime, such as, for example GPS coordinates, thermal data, still or video image data, and audio data. Further, as described, such data might, in real-time, be transferred from one mobile device 100 to another mobile device 100, or from one emergency database 202 to another emergency database 202. This data might be transferred by cellular, satellite, wireless, wired, Internet, or any type or combination of data transfer. Thus, integrated emergency database 202 might collect synchronous and asynchronous information regarding a crime scene or emergency situation from one or more mobile devices or other sources in a specific physical range, for example, a campus or a given building on a campus.

Also shown in FIG. 2 is Security System 222, which might be a residential or commercial security system employed in, for example, a home, educational, institutional, or business structure commonly used to monitor for fire, power outage, break-in or similar events. Such systems are often separately wired to central monitoring, in communication to central monitoring through telephone lines, and possibly backed-up to central monitoring through cellular connection. Consequently, emergency events detected through security system 222 might be communicated to integrated emergency database 202 for processing and/or forwarding to mobile devices 100 and/or 212; and emergency events detected and communicated to integrated emergency database 202 by, for example, mobile devices 100 and/or 212, might similarly be forwarded to security system 222.

Integrated emergency database 202 might also allow law enforcement agencies or other emergency responders to inform other mobile devices in a given geographical region or specific location or building within a campus. Thus, a campus security force or a law enforcement agency might transmit an alert to one or more mobile devices in a given location to inform the public of an emergency situation, for example based on an emergency alert generated by mobile device 100. For example, an emergency dispatcher might receive numerous emergency alerts from mobile devices in one or more regions. Each region might have a corresponding emergency database to accumulate similar evidentiary information from mobile devices employing embodiments of encapsulator 130. The emergency database might process data input from the one or more mobile devices to determine whether to send alerts or other data to other mobile device users in the region, or a portion of the region. For example, the emergency database might send data such as locations of nearest building exits, travel directions to avoid an emergency, medical or lifesaving information for assisting wounded people, the location of a closest police station, fire station or hospital and other data.

Described embodiments provide a system for alerting emergency responders to the existence of an emergency situation. The system includes multiple mobile devices in communication with a mobile communications network. An emergency database, such as integrated emergency database 202, sends an emergency alert notification to one or more alert groups associated with the users of each mobile device in alert mode. Each mobile device sends an emergency alert notification to one or more additional mobile devices in a predetermined physical proximity to the mobile device. Various servers could be customized in order to increase emergency alert protocols and responses. Each mobile device is capable of seamlessly interfacing customized emergency alert situations for school campuses, corporate complexes, industrial centers, governmental buildings, retail developments, cities, municipalities, sports stadiums and other organizations or properties (generally, a "campus") topographical and geographical perimeters. The general public mobile alert system automatically converts when crossing the established geographic perimeters to a mobile alert system designed specifically to a particular campus. Each mobile alert system program can be tailored to the "campus" protocols, specific security requirements and the campus emergency responder access and response.

In the case that the customized program is only relevant to a select group, this select group might be provided a method of unlocking these features or otherwise having the customized program provided to them in a secure way. An overlay of the emergency "hotspot" with an emergency locator icon over the campus map can include, but is not limited to, buildings, building interiors, parking lots, parking garages, walkways, landmarks, stairwells, elevators, highway mile markers, land contours, trees, lakes, ponds, points of interest or significance. Described embodiments include a server and database that is in communication with the mobile communications network and servers on the campus.

Some embodiments include a method of reading, storing, and recognizing biometric identifiers to prevent a false or accidental alert, and to ensure that the correct individual is sending the alert. The virtual emergency GPS application automatically calculates longitude, latitude and vertical height of structures within the campus grid and campus perimeter. The personal mobile device has the capability of triggering various sirens when authorized by The Mobile Safety Management Software Program (MSM). The personal mobile device might interact (in conjunction with a server/database) with surveillance or security cameras near the "hotspot" emergency location in order to capture and time stamp the event and send this information to the appropriate emergency responders, authorities, or other concerned parties. In addition, the personal mobile device might have the ability to direct the focus and position of surveillance cameras that are capable of panning.

Described embodiments include an emergency witness icon that when accessed distinguishes alerts sent by a person witnessing an emergency from alerts sent by a person directly involved in an emergency. In addition, in another embodiment of the current invention, layer socket technology could be employed with or without the personal safety device application being open. In this manner, the inside perimeter of the campus could track users within the campus network. Additionally, the MSM could be an open platform accessed by and customized by all campus organizations. It is obvious to anyone familiar with the art, that even though the MSM platform and architecture could be open to any entity, each will have security firewalls protecting their campus and individuals within the campus grid.

Figure 3:
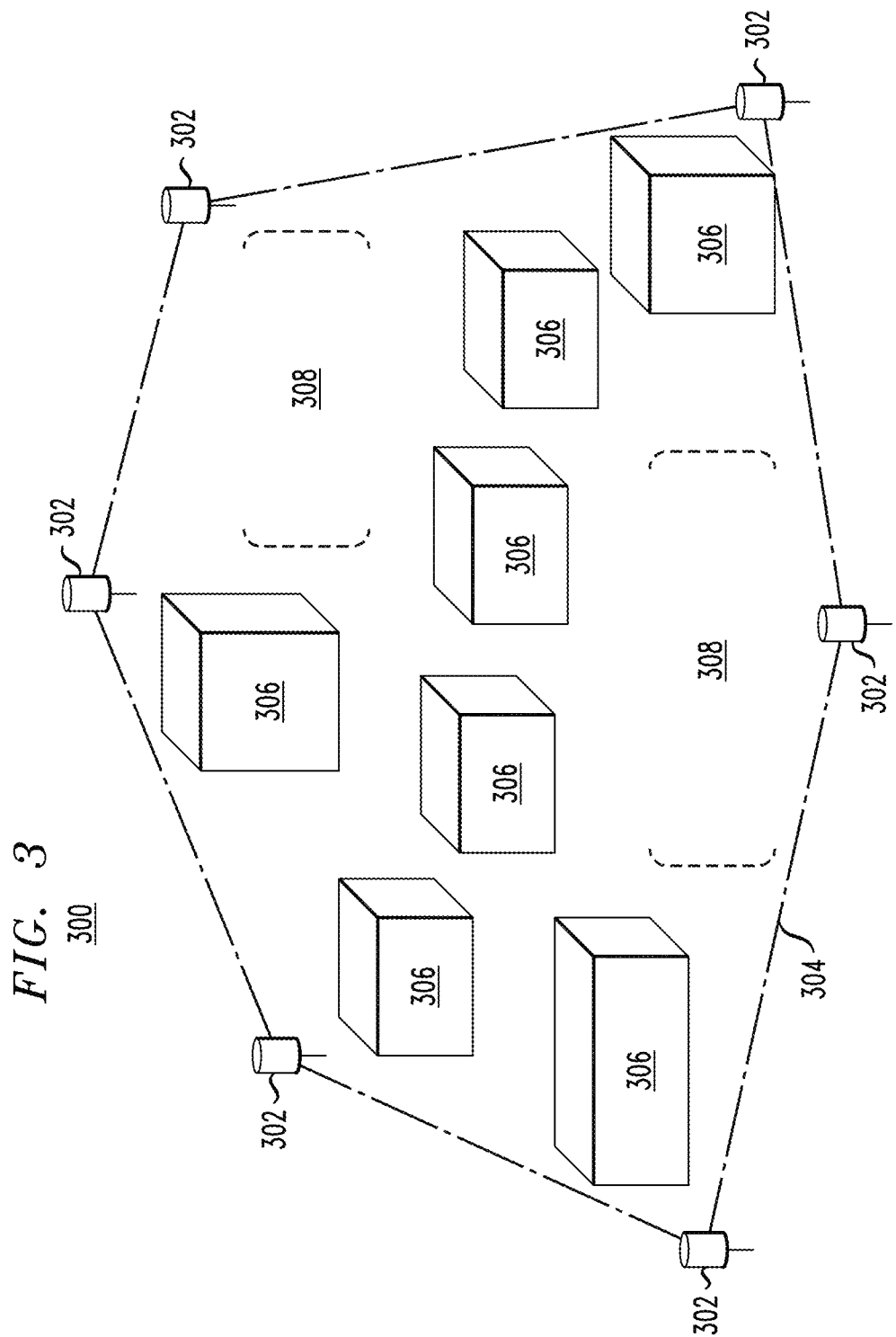
FIG. 3 shows a block diagram of a physical campus having an outside perimeter and a geography plat, in accordance with embodiments of the present invention.

FIG. 3 shows a block diagram of an exemplary virtual representation of physical campus 300 having outside perimeter 304. Outside perimeter 304 might be set by one or more dynamic X-Y perimeters 302 to establish a GPS perimeter of campus 300. XY coordinates of campus perimeter 304 are entered and mapped outlining the outside perimeter in every direction. The perimeter of campus 300 might be defined as, for example, the property line which borders non-campus property. As shown in FIG. 3, campus 300 might be represented by a campus map and topography with buildings, structures, roadways, sidewalks, parking areas, etc. (shown generally as structures 306 and areas 308). Campus 300 might generally be at least one of an university or school campus, office complex, company headquarters, industrial park, sports stadium, retail shopping complex or mall, cities buildings, a park, or any other such geography.

XY location data and GPS coordinates for campus perimeter 304 are communicated to and stored on a server, for example integrated emergency database 202, for communication with an individual's smartphone and or mobile device application. The campus buildings, parking lots, structures, sidewalks, roadways and other geographical features are superimposed within the virtual XY perimeter as shown by structures 306 and areas 308. When a smartphone user drives or walks through XY perimeter 304 established by one or more dynamic X-Y perimeters 302, the general personal safety mode and icon displayed on the smartphone (for example as described in regard to FIG. 5) could change to an emergency icon with a logo corresponding to the owner or operator of the campus. The icon might change back to a general public alert icon when the mobile cellular device again crosses XY perimeter 304 when exiting the campus. The smartphone, for example by employing GPS transceiver 104, might detect passing through the campus perimeter when traveling into the campus and could superimpose the campus map based data of the mobile device. The campus map might be transposed with the emergency alert emergency "hotspot" overlay.

When the campus perimeters are entered by the organization, the GPS grid within the perimeter might be controlled by the campus servers, remote servers or combination of both. One or more servers will dynamically control the data, which could be sourced in any format, protocol and technology. In addition, various campuses could require a different set of rules unique to their emergency needs. The MSM, Mobile Safety Management software program could be used to customize safety criteria and functionality by the campus administration in order to better serve the campus police and the student body. The MSM software will be networked and linked to one or more servers. The MSM system could be an open platform for schools, corporations, industrial parks and other organizations could use when incorporating the personal safety network for their campuses.

Table 2A-2H shows terms employed in the MSM system:

TABLE 2

| Mobile Safety Management (MSM) Software Platform | | |
|---|---|---|
| A. GPS Perimeter and Campus Grid | | |
| Virginia Tech | Latitude ° | Longitude ° |
| Perimeters: Campus A | 37.23, 37.33, 37.78, 36.11 | 80.42, 78.63, 74.98, 73.22 |
| Campus B | 34.33, 35.67, 34.91, 34.38 | 83.22, 84.99, 84.02, 85.00 |
| Conversion Long/Lat to GPS | objFix = gps.Parser.getgpsfix | objFix = gps.Parser.getgpsfix |
| | objPos = objfix.position | objPos = objfix.position |
| Structural Elevation | 4 Levels-School of Business | GPS Height Conversion for each |
| Conversion to GPS-enter | meters. | Level-School of Business |
| elevation plat and building | Level 1-1.905-6.858 | (Hendry Hall) |
| levels height for all structures | Level 2-7.7144-11.0947 | L 1 −0,031.0012 |
| on campus. | Level 3-12.0091-15.8800 | L 2 −0,021.1725 |
| | Level 4-17.1602-20.8788 | L3 +0,018.0042 |
| | | L4 +0,012.8781 |
| B. Emergency Submenu Icons | | |
| Gunman | Fire | Robbery |
| Allow Siren Trigger / | Allow Siren Trigger / | / Disallow Siren Trigger |
| Bomb | Assault | Accident |
| / Disallow Siren Trigger | / Disallow Siren Trigger | / Disallow Siren Trigger |
| Murder | Help | Suspicious Person/Car |
| Allow Siren Trigger / | / Disallow Siren Trigger | / Disallow Siren Trigger |
| C. Enter Student Emergency Contact Data and ID | | |
| Student ID # | Emergency email address | Smart Phone # |
| 12634-80-85734 | sam12634-8@vt.ed | 804-555-1234 |
| | Enter Faculty and Staff | |
| D. Enter Dispatch Unit Data | | |
| Campus Police | Richmond Police Backup MSM | Richmond Fire Department |
| 911 directed to Campus Police | 911 directed to other law enforcement | 911 directed to the fire department, ambulance |
| E. Enter Buildings Emergency Exits for Guidance System | | |
| School of BUS | Exit Map | |
| School of ENG | Exit Map | |
| F. Enter Encapsulation Criteria | | |
| CAD/server-Accept Video | CAD/server-Accept Audio | CAD/server-other in the field data |
| CAD/server-Time Stamp | CAD/server-Wireless Mesh Backup (See FIG. 11) | mobile device emergency override on/off |
| G. Internet and Technologies | | |
| Server Requirements | Wireless Internet | Mesh Network Capabilities |
| Carrier's Cellular Phone | Redundancy Systems for an | Computer Aided Dispatch |
| Signal Strength | Emergency Alert | Protocols |
| Bandwidth | Data Emergency Capacity | Patrol Car Interface/EMG CAD |

TABLE 2-continued

Mobile Safety Management (MSM) Software Platform

| Encryption Security | Digital Biometrics (Digital Finger Printing) Cellular Phone | Digital Biometric Database for all Participants |
|---|---|---|
| Commercial, Industrial, Retail, Gov., School, etc. Specs | International Adjustments and Protocols and Specs | Customized Personal Safety Applications and Networks |
| | H. Participants Usage MGT | |
| Regulations/Integrity | Penalties of False Alarms | Access Restrictions/security |

Table 2A shows that the MSM software determines the campus GPS perimeters and sets the boundaries of the geographical grid of the campus within the outer perimeter. The inner grid defines a protected zone subsystem. One or more parameters, such as height, for each building or other structure of the campus could be provided to the MSM to calculate a Z coordinate in order to demonstrate the size, shape and architecture of structures as well as the locations of various levels within the structure and the location of the emergency within said structure. The MSM software automatically maps out the perimeters through the data point locator entries as well as include all the inter campus grid within the established perimeters. The embedded or correlated geographical data might be stored in a multitude of formats including but not limited to, Static and Kinematic pseudo-kinematic, GPS and Pseudo-static GPS, TECEF coordinates (Cartesian coordinates, Earth Centered, Earth Fixed Rectangular coordinate system) etc. The campus grid map showing all structures and real time X-Y-Z emergency hotspots could dynamically determine the precise location with great accuracy of the crime or emergency not only within the parameters of the campus but also within the interior of any structure on the campus. In case of an actual emergency, the alert symbol might be displayed on the campus GPS, Z factor map.

Table 2B shows that the MSM might have one or more customizable submenu icons, which might be determined by the campus authority. For example, in use by the TSA, an airport map could become the campus, with its own set of criteria. In addition, in yet another embodiment of the invention, the TSA authority could customize specific safety requirements and submenus. A TSA submenu could include other variables such as [Unidentified Bag] for example, as well as other specific emergency criteria and rules established by authorities when utilizing the MSM software program. In addition, in the case of a corporation, the submenu could include [Travel Mode] which could automatically or manually adjust to new emergency dispatch numbers and other applicable protocols when traveling within another country. In addition, various features could be allowed or disallowed, such as the ability of the mobile device to trigger an external alarm siren based on the appropriate emergency.

Table 2C shows the ability of campus administrators to enter personal and professional information, details, profiles, and identifiers related to the student body, faculty, administration and staff personnel. This includes a record of digital fingerprints or other biometrics which will be embedded into the users mobile device in order to prevent false alerts, email contacts, student ID's and faculty ID's, cell phone numbers and other emergency identification and contact numbers. This is not limited to a scholastic setting, as the same process could be applied in corporate settings, government settings, international settings, large public events, industrial complexes, retail environments, etc.

Table 2D references the emergency responders, campus police, local police departments, EMT's, paramedics, emergency room staff, fire departments, etc. The MSM system allows accounts for emergency call redundancy, backup police units and other criteria. Table 2E references the ability to include an automated guidance system capable of directing individuals on campus away from the scene of the crime or emergency, exit areas and the most efficient escape to safety. For example, if a 5 story office building is on fire, there might be limited routes for escape from the 4th and 5th floors. In such an instance, the MSM might provide an exit map showing the route for exit is the southwest stairwell to the third floor where victims must stop descending, cross the room to the northeast stairwell and continue down. The MSM system could provide directions, and a map showing the path they must take to escape. In one embodiment, information on the safest escape route could be provided to the current invention by those who have effectively escaped to a safe location. Upon their exit from the structure those who have successfully escaped will be prompted to provide the details concerning the route they took when escaping. These details, as collected from a growing number of escapees will be averaged and updated in real time to provide the best and most up to date information to those who are still in danger.

As the emergency progresses, alerts are sent, emergency responders provide information, and information is presented to those in danger dynamically and in substantially real time. The emergency information could be provided in several forms to those in danger. For example, some described embodiments might provide information to those in danger in the form of maps, schematics, lists of recent alerts, or messages or instructions from emergency responders. In cases in which it is important for law enforcement, medical responders, firefighters, etc, to send instructions or messages to potential victims, these instructions might be provided in the form of maps, text messages, verbal recordings, video recordings, etc. In yet another embodiment, emergency responders could remotely access one or more mobile devices within a determined physical range of the emergency situation, activate the devices' speaker phone features, and make a verbal announcement that could be heard from any phone in the area at the same time.

In another embodiment, emergency responders might have the ability to remotely access the receiver and/or camera of every mobile phone in the area effectively remotely recording the audio and/or video input from one or more phones in order to assess a situation, gain information and encapsulate evidence. Further, the remote access to mobile devices through the server might also include the ability to turn the phone on if it is off, as well as adjust volume and vibration controls, and change any settings on their phone. This might be particularly useful to alert individuals of an emergency since, for example, many people might turn their phone off or ringer/vibration off when in a meeting or classroom and would otherwise not be able to be warned. In another example, if there is a violent attack in a 5 story office building, as reports of the attacker's location are made, the location of the attacker could be updated on the map displayed on a user's smartphone. If two or more reports of the attacker occur at the same time or in close succession that report the attacker in two relatively distant locations at the same time, the MSM program could warn of the possibility of multiple attackers.

In addition, the MSM might determine an estimate of the ongoing emergency scenario in actual-time as the data emergency data is transmitted from various "hotpots" sites. In a scenario in which at least one attacker has been reported but there are other conflicting reports that seem to indicate another attacker or threat, those conflicting alerts might be recognized by the MSM program as being potentially related but potentially separate. The MSM program displays the locations of threats in their suspected locations and updates those locations as new information comes in. Older threat location information will still appear on the map but might be displayed in a different color or be displayed differently than recent threat location reports in order to distinguish between the two. As more reports and information comes in, the location information that is determined to be too old or now irrelevant is removed from the map but could still be found in a browsable list or log of all of the alerts (updated in real time) in the order in which they occurred.

To continue the example, ten people report that there is an attacker on the 5th floor of the building. As the attacker walks about the floor and is seen by additional witnesses, the witnesses send alerts, and the location of the attacker is updated on the map displayed on users' smartphones. If the attacker was last reported to be at the southeastern end of the 5th floor, and an alert comes in relatively a short time later that a attacker was seen in the middle of the 3rd floor, this is a condition where an alert possibly conflicts with the previous alert since the two alerts describe the attacker in 2 relatively distant locations within a relatively short time period. The MSM program might measure distance within buildings by taking into account walls, obstacles, locked doors, and other factors that must be taken into account when calculating the average amount of time it takes to travel on foot within a building or structure. Given this information, the MSM program might make estimates as to whether or not possibly contradictory reports may be either false or separate threats. In the example of two reports of an attacker being on two different floors, the MSM program might display the threat location with the largest amount of corroborating reports in a different manner than the conflicting report. As more reports come in that corroborate the originally conflicting report, the MSM program might display the report as a confirmed threat. The MSM program might constantly measure the threat level of a location against time and new reports and information. For example, as emergency responders confirm that certain threats are eliminated, the MSM might lower the threat level accordingly. As time passes and less reports are made, the MSM might adjust the threat level accordingly and in a manner appropriate to the nature of the emergency.

Table 2F refers to the MSM software's ability to provide customizable criteria of various features which could be activated or not activated depending on, for example National Emergency Number Association (NENA) 911 standards, such as a computer-aided dispatch (CAD) system and capabilities. Table 2G references various technological criteria that might be needed on the campus in order to allow the system to be optimally utilized. In addition, smartphone technology advances will work in tandem in providing a first response from the field to other smartphones and students prior to the law enforcement ability to get to the scene of the crime. Described embodiments provide first response capability that stems from citizens, coworkers, students instantly informing others of a dangerous situation preventing the loss of life. Table 2H references the capability of MSM alert rules and regulations of local, state and federal laws, access restrictions, IT security and other information regarding individual rights. In addition, students that don't have smartphones could still be contacted by SMS or calling.

The secure MSM program might be implemented having an open architecture with a software platform capable of dynamically integrating with any emergency call center, response center, municipality, educational facility or district, corporate entity, industrial complex, resort area, city and rural geography, governmental complex or any and all customized mobile emergency needs designated by factors described therein. The campus server could interface the MSM server through password security and firewall thereby not allowing unauthorized access to protected and sensitive information.

Figure 4:
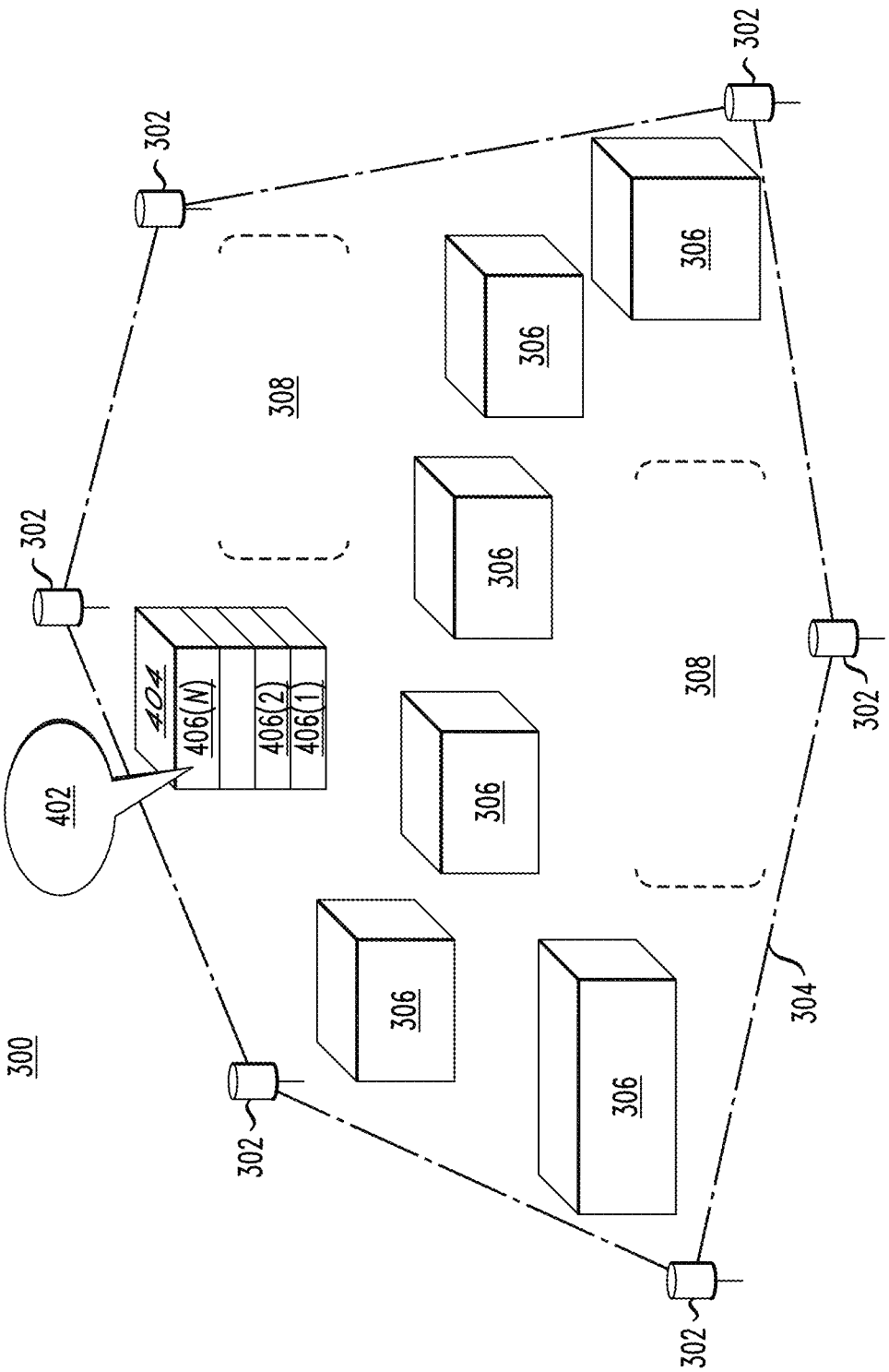
FIG. 4 an exemplary location of an alert "hotspot" within a building of the campus of FIG. 3, in accordance with embodiments of the present invention.

FIG. 4 shows the exemplary campus map of FIG. 4, having an alert message 402 displayed at building 404, having floors 406(1)-406(N), where N is the number of floors of the building. The Z factor as illustrated when activated, might store such data leading up to, and during, the activation of an emergency alert mode of mobile device. As shown in FIG. 4, building 404 has an emergency alert 402 indicating a location within the building that is the location of the emergency. Alert 402 might be displayed as a report that could include, but is not limited to, the time the alert took place, the nature of the emergency, the identification of the sender, the identification of the person in the emergency if different than the sender, the number of people involved in the emergency, the location of the emergency if different than the location from where the alert was sent, whether or not the emergency has been resolved or is pending, among other data. The report might be displayed on the map or in a list of recent alerts as a summarized version to save screen space or expanded on command to describe the alert in greater detail and provide other information or features. For example, the image of the building might be expanded to show the interior details and the location of the emergency.

For example, on Apr. 16, 2007, Seung-Hui Cho was a gunman involved in a massacre on the campus of Virginia Polytechnic Institute and State University in Blacksburg, Va., killing 32 people and wounding 25 others. To use this tragedy as an example, the shootings occurred at 7:15 AM and again at 9:40-9:51 AM. In this event, at 7:15 AM, several people were shot or killed, yet the gunman continued to kill others over two hours later. Described embodiments might allow students to escape such a would-be assailant with real-time reports to other students through the mobile safety social network prior to the reaction time of authorities getting to the scene of the emergency. In the real-life massacre, police required over 6 minutes to get to the second murder event that killed 30 additional people. In this example, described embodiments might have provided a first line of defense emergency network with alerts originating from the victims or witnesses and providing a unified mobile safety network that could pinpoint the building and even the level of the building in which the shooting took place. Superimposing the campus map with the alert signal, visually warns the student body where an emergency is happening, and how to best exit the building. Emergency personal will benefit in like manner and know the assailant's whereabouts is on the Nth floor as shown in FIG. 4.

Some embodiments of the present invention might include an ability of a mobile device to scan a specific room or small area to identify active mobile devices in the room and to electronically tag an assailant. By tagging the assailant, the assailant's mobile device might be tracked and denied information provided to victims or other users in the area, and the assailant's mobile device might be deactivated or otherwise controlled remotely. Such ability of the mobile device might prevent an assailant from using information provided to victims or other users in the area as an aid for further criminal activity or to escape law enforcement.

Figure 5:
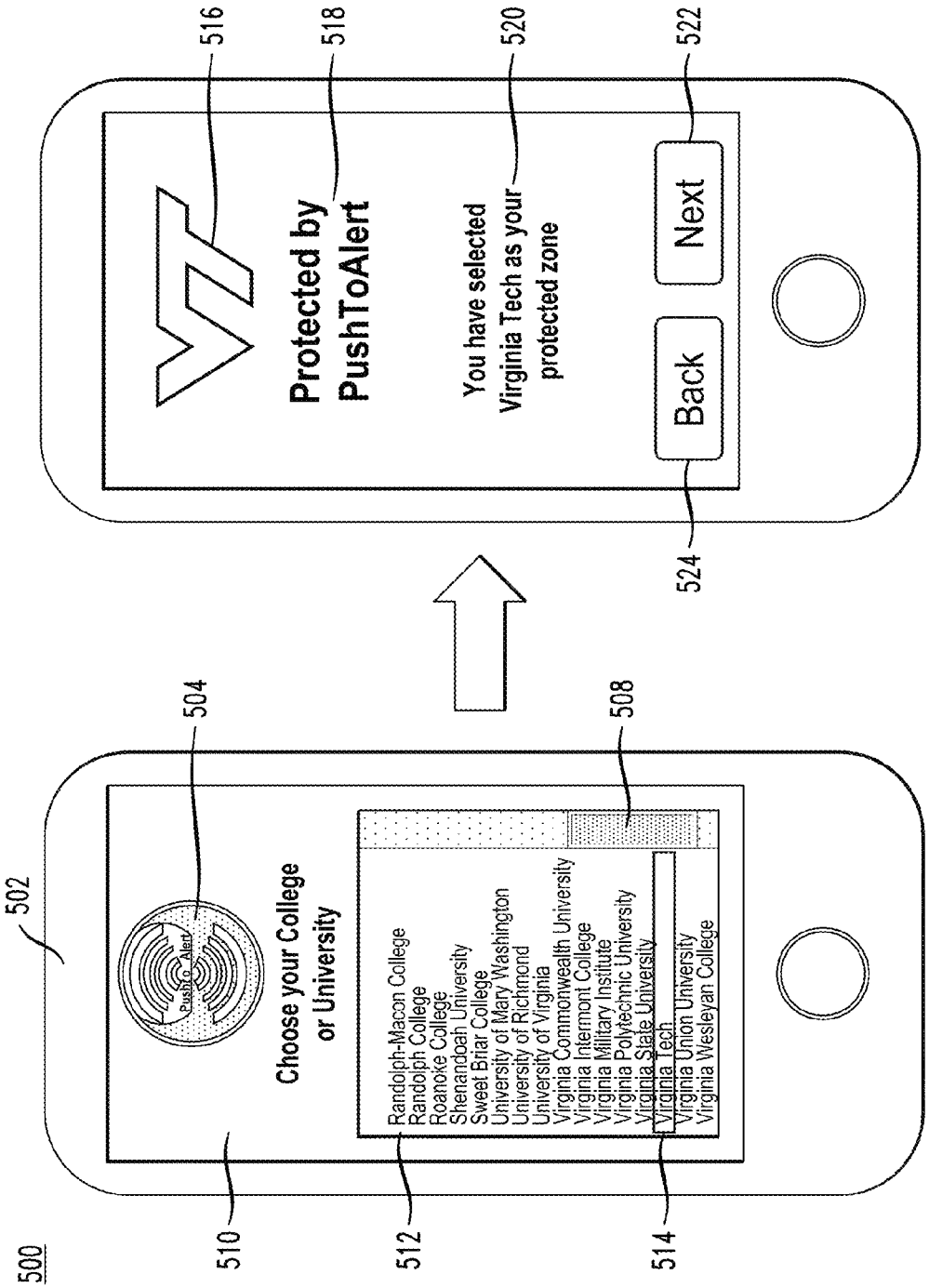
FIG. 5 shows an exemplary consolidated campus mobile alert console, in accordance with embodiments of the present invention.

As described herein, the XY threshold crossing border line demarcation could convert the general public alert to a specified location's geography. In this example, a consolidated console database listing could be selected, such as shown in FIG. 5. FIG. 5 shows mobile device 502 which might typically operate such as described with regard to FIGS. 1 and 2. The school emergency alert environment for example could exemplify a consolidated listing of all participating colleges of a mobile alert system 504. The MSM software program will allow access of an assortment of enlisted school downloads selected through selection bar 514. In this case the selection of university in alphabetical order adjusting to screen size started with the screens scroll of enrolled campuses, shown as Randolph-Macon College to Virginia Tech in selection window 512 having scroll bar 508. Virginia Tech was selected, shown by icon 516, and GPS and XYZ perimeter data and campus grids might be downloaded to mobile device 502. The Virginia Tech selection becomes a protection zone corresponding to mobile device 502, as indicated by message 520. Buttons 522 and 524 allow a user the option to choose other protected zones or to continue.

For example, students, faculty, administration and staff scroll through college listing 512 with scroll bar 508 and select their school with selection bar 514, download the MSM software and campus data, answer security questions and password protection to verify they are authorized to access the campus data, for example, by providing a student ID number or other identification. The user might then proceed to scan their fingerprints making a digital fingerprint file which is sent to the server for storage and cross verification. As described in greater detail with regard to FIG. 7, the fingerprint and biometric identification might help to reduce or prevent false alarms.

The personal alert network described herein might be applied across various specialized industries and personal alert networks. As shown in FIG. 6, another embodiment might interface various security access and retrieval systems used, for example, real estate agents. Several companies currently manufacture a lockbox similar in function to the one shown in FIG. 6 as lockbox 604. The personal safety alert system and network might be utilized in conjunction with a smart real estate lockbox. In addition, it is understood by anyone familiar with the art, that multiple platforms, cellular networks, various industrial and commercial safety applications could be customized with its own set of functions and design specifications. Currently, real estate lockboxes record authorized entrances of the home or commercial building and timestamp trace and store the data. A real estate lockbox is a padlock shaped box that hangs around the doorknob of commercial buildings and residential homes providing secure access. The device holds the keys to a house in order to allow real estate agents communal access while continuing to keep the property secure. The lockbox opens for a real estate agent when the agent has entered their password to get into the house. Real estate lockboxes are secured either with a manual key, a security code, or a magnetic strip card reader. In accordance with a described embodiment, lockbox 604 might provide homeowners with notifications to know when the home has been accessed and by whom.

A given real estate agent might require a password to be updated over, for example, a telephone modem. In addition, remote access to a lockbox through, for example, a cellular network using a mobile device could access a shackle code generated for the real estate broker. Various Mobile devices might remotely open the lockbox in order to obtain the key using inferred or other wireless signals through a cell phone adapter. In addition, the lockbox and server might track all accesses points through the cellular network.

Real estate agents often meet total strangers at property sites and are subject to dangerous situations. Described embodiments of the current invention might provide real estate agents with first line of defense protection by simultaneously alerting emergency responders while triggering a siren built into the lockbox as shown as siren 608 to emit emergency alarm sound 606. In addition, a real estate agent could inform other agents, people generally within the area, and emergency responders through the emergency alert messages provided by the personal mobile safety network as described herein. Both the real estate lockbox shown in FIG. 6 and the personal mobile device could trigger the built in siren through the adapter device and or mobile devices. The lockbox, adapter or mobile device could be equipped with any wireless protocol such as Bluetooth®, 802.11 WiFi, or other triggering mechanisms. Security camera 612 might be activated remotely by the real estate agent or other authorized individuals. In addition, security camera 612 might be activated remotely or through a motion control sensor option by the real estate agent or other authorized individuals. Collectively, alert smart lockbox 604 interfaces with the mobile safety device, dedicated servers and cellular networks, wireless and wired networks or any and all combinations thereof. In addition, a security company's logo could be on the lockbox (shown as logo 610) signifying the fact that this unit is armed with the mobile safety network.

Integrated emergency database 202 might include various biometric databases, which interface with various triggering devices incorporated in Personal Mobile Safety software on smartphones and other mobile devices. FIG. 7 shows an exemplary fingerprint scanning screen of a mobile device in accordance with described embodiments. During setup, the mobile device user creates a password that is entered in order to alter the program's features. Once the correct password is entered in the setup screen, the user scans his/her fingerprints on grid 704. The identifying information relating to these fingerprint scans is saved on the mobile device and the server/database 714 (which might generally function as described in regard to integrated emergency database 202) and stored securely. Erasing the fingerprint or other chosen biometric identifiers might disarm the personal safety alert program and disallow alerts to be sent. An individual scans each finger on the mobile device within grid 704 until each are complete. When on the main screen of the program, access to the area of the program that sends alerts is granted only to the individual whose fingerprint matches a fingerprint on file. The icon on the main screen of the program 712 scans the fingerprint of the individual pressing their finger on the icon to open the program. If the fingerprints do not match a fingerprint on file in the mobile device, access to the portion of the program capable of sending alerts will not be granted. This feature helps prevent false alerts from being sent. The biometric identifiers are not limited to fingerprints. Facial recognition, voice recognition, retina scanning, and other biometric identifiers and any combination of biometric identification methods could be incorporated into the current invention. In addition, voice recognition and voice activation could be used to operate the program and send alerts therefore eliminating the need to interact with the program by physically touching the mobile device.

In one example, fingerprint-triggering verification with the secure biometric database could help prevent false alerts. If a person steals the mobile device and tries to trigger the alert as an aversion it would not react since his biometrics are secure and embedded and linked to the mobile device and central server. In addition, these secure alert triggers might also allow law enforcement agencies or other emergency responders to prevent false alarms and disallow misinformation between mobile-to-mobile devices. Thus, a campus security force or enforcement agency could trace the originator of the emergency alert through the current invention by utilizing this tamper proof biometric verification system preventing false transmitted alerts. A similar mechanism is not limited to home and commercial alarm devices and all related remote access devices which arm, disarming and monitor a home, building or device through this setting as shown by 702 and 704. Exemplifying this sector of the present invention, 704 scans authorize the fingerprints linked to the phone number and registration. Fingerprints or other biometric identifiers securely store the biometric alert trigger tailored only to the mobile phone's owner or user. If the fingerprint doesn't match the authorized biometric the push button alert device will not activate. If the authorized and registered (campus database match etc.) does match the alert will result in culmination of the alert process.

Figure 8:
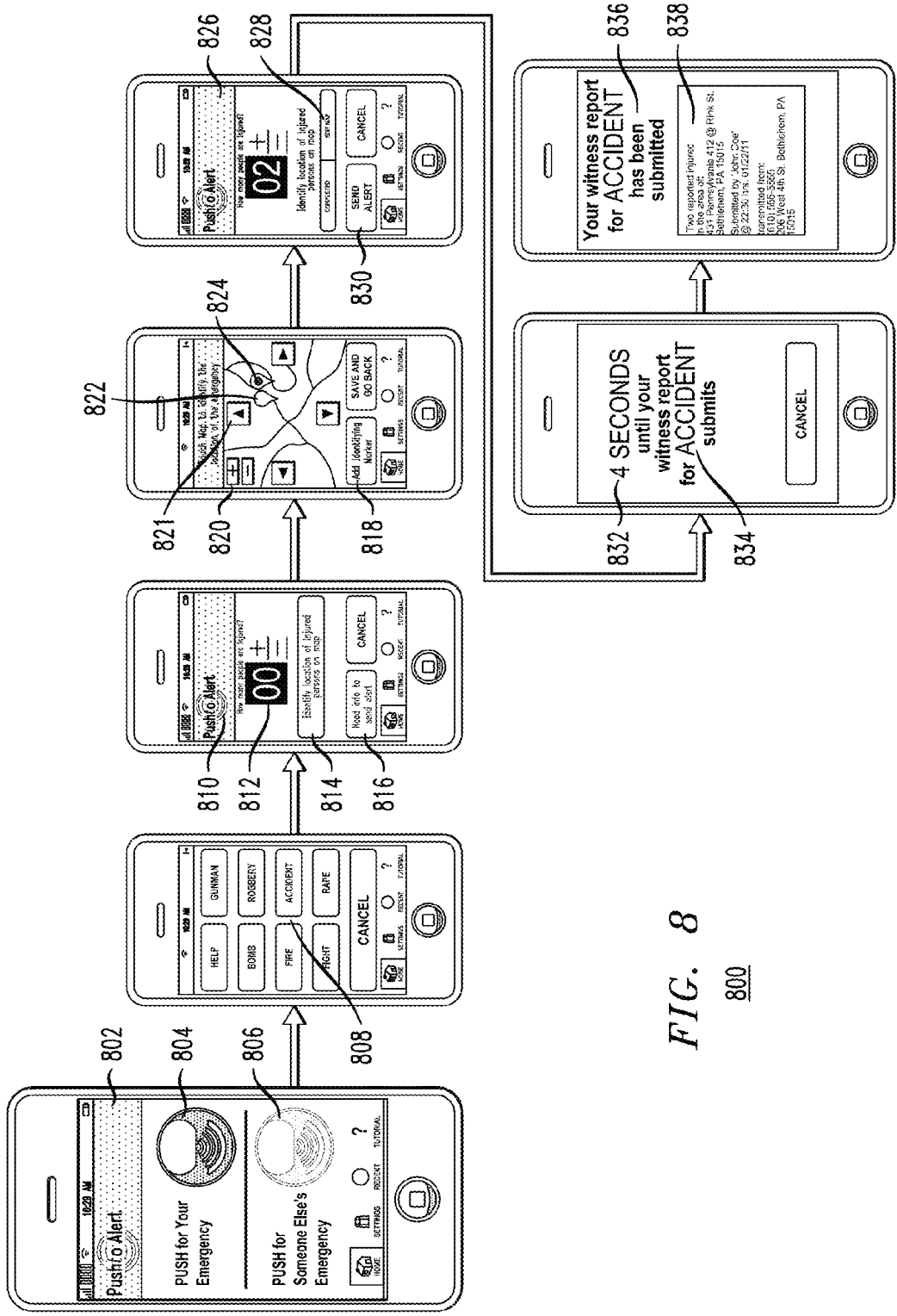
FIG. 8 shows an exemplary witness application, in accordance with embodiments of the present invention.

FIG. 8 shows an exemplary embodiment of the present invention where a user can report witnessing an emergency situation. As shown in FIG. 8, button 804 and button 806 provide a choice of distinguishing your emergency from someone else's emergency to distinguish whether you are directly involved in the emergency or an observer of the emergency situation. The same biometric technology as described with regard to FIG. 7 might apply to the witness icon. Button 806 shows a separate icon regarding the alert witness protocol. Screen 808 distinguishes witness alerts from emergency alerts sent by those in immediate danger and specifies the emergency situation through one of the submenu icons. Page 810 is where the witness is able to specify the number of people in danger (page area 812) as well as their respective locations (page area 814). Page area 812 is an area where the witness can enter the number of people that are in danger. Page area 812 might be used to demonstrate the number of threats or number of general emergencies if the emergencies are separate in nature. For example, a witness may see two cars in a head on collision, but may not know how many people are in the cars. In this example, the witness would use 812 to note that there are two cars and thus two emergencies.

Entry "button" of page area 814 is used to proceed to a map screen where the user's GPS location is shown (marker 824) and one or more emergency markers (emergency marker 822) can be placed to indicate the location of the emergency. Zoom buttons 820 allow the map to be zoomed in or out, and arrow buttons 821 allow the map to be panned. Entry "button" of page area 818 allows a user to mark multiple locations of emergencies through the assistance of the GPS map. Thus, as described, the witness could approximate through a GPS location map where the emergency is or as previously described in this current inventions previous filings; using sensors to calculate distance and XYZ coordinates of the emergency. Entry "button" of page area 818 allows the witness to add an identification marker to the scene of one or more emergencies on the GPS location map. This could provide to emergency authorities information regarding the crime or emergency such as a type of emergency, a number of people involved, and the location. The added witness icon will allow police, firemen and other emergency authorities to contact the witness or witnesses in order to gain valuable information regarding the incident. The map itself could be provided by one or more online mapping services, such as Google.com and Mapquest.com.

It is understood by those skilled in the art that color alert distinctions could be variable in order to symbolize various situations. For example, emergency marker 822 might be flashing when the emergency is ongoing and in progress and stop blinking when the situation is resolved. Blinking, flashing, moving, animation, images, videos, separate colors, and distinctive and separate shapes could be incorporated into the alert marker icons in order to distinguish a witness from a person directly involved in the emergency. A user might use an image of themselves to act as a marker on a map in order for emergency responders to better recognize said user. Conversely, a user could also use an image of a criminal, emergency threat, witness, person of interest, or object of interest as a marker on a map to better assist emergency responders. After a witness enters information into page areas 812 and 820 (e.g., the number of people involved and the location of the emergency). Entry "button" of page area 816 is activated to become button 830 to send an alert. Without the required fields completed an alert cannot be sent, as indicated by button 816 displaying a message that more information is required.

Displays 836 and 838 display an exemplary emergency report to the witness that indicates the alert has been submitted and summarizes the information provided by the witness (e.g., the number of injured in the report, the location, and the transmission numbers for both emergency authorities and the witness for future questions, evidentiary information and eye witness requests). Display 834 gives a user an option to cancel an emergency alert before the alert is sent, for example, to emergency authorities and/or one or more individuals in the user's mobile safety network list. It is understood by those skilled in the art that when setting up the features of the program in the settings screen, users could distinguish and prioritize notification protocols. In other words, a witness of a crime or emergency could distinguish between people directly involved in the emergency and their respective locations. In addition, a flexible dynamic prioritization algorithm could distinguish various mobile alert groups in the order of priority, message and distinction. The MSM software might also distinguish between witness and evidentiary information from directly involved secure evidentiary encapsulators.

As shown in FIG. 9, described embodiments might allow mobile device 902 to remotely activate one or more security peripheral devices, such as a siren or security and surveillance cameras, shown as 914, as indicated by remote control signal arrow 906. The emergency alert is also sent to central server/database 910, as indicated by signal arrow 908. Security camera 914 might automatically transfer video and audio footage to a central server/database 910 (which might operate similarly as described for integrated emergency database 202). Mobile device activation of remote video units in proximity of the emergency might help emergency responders pinpoint time of the emergency through the assistance of general citizens witnessing the emergency or directly involved in an emergency. Video data 912 might be streamed to emergency dispatch units through central server/database 910 or to other emergency servers and databases. The emergency is therefore captured and time stamped and stored in central server/database 910 to assist authorities with any future investigation. In another embodiment, a mobile device might remotely control the position of security and surveillance cameras that have the ability to pan or move through remote control, based on the XYZ positioning of the mobile device(s) 902 triggering an alert.

FIGS. 10A-10C show exemplary diagrams of wireless alert triggering and surveillance mobile device encasements that might be stealthily attached to clothing garments, key chains, purses, handbags, or other accessories and be made to look like discrete and common items. An example of such a device would be if it were encased in the shell of, or otherwise designed to look like, a pen. The devices could be wireless and interface the smart mobile device or directly contact and trigger the alert to emergency responders. 1002 indicates a wide-angle camera that could be activated in order to interface with various mobile devices and could interact with the MSM system interface and utilize facial recognition technology and could access a central server/database. It is understood by anyone familiar with the art that the camera could be activated by motion and could utilize night vision technologies. 1008 indicates an audio microphone capable of encapsulating audio data from the scene of an emergency. 1004 indicates various attachment devices that could connect the mobile device to a purse, lapel, jacket, shirt, coat, bracelet, necklace. This device could be very small and be embedded and hidden within garments or accessories of any kind.

1014 indicates an attachment between the micro surveillance devices with a mobile device or computer that incorporates a foldout screen display 1020 which might be a touchscreen capable of receiving touch input and displaying color video and images. Thus, 1014 might be capable of playing audio, receiving voice commands and other general functions of a computer tablet device or a smartphone. 1018 indicates a pull down mechanism which holds the foldable digital display and stabilizes the screen making it capable of unfolding many times the size as a fixed display screen. In this manner, a stealth personal safety device could perform like a full screen computer tablet with mobile cellular phone capacity. In another embodiment license plates could be surveyed, photographed, recorded and encapsulated in a smart database for police authorities.

FIG. 11 shows an exemplary street with various commercial, retail, government or other types of buildings 1102, and residences 1104. Lines 1106 indicate a sidewalk or other pedestrian walkway, and lines 1108 indicate a road, driveway, street, or other vehicular path. As a user passes each building 1102 and 1104, a dynamic report could be generated on the user's mobile device that could evolve in real time as surroundings change. This dynamic report could include, for example, geographically historical crime data pertaining to each XYZ coordinate. As the mobile device passes through any geography on a map (including the interior of buildings and other structures) reports could appear on a display showing historical crime statistics and other important safety information or instructions pertaining to the respective area the mobile device happens to be located as well as areas within the immediate direction the device is moving. In addition, the crime database (e.g., integrated emergency database 202 or central server/database 910) is scalable and building graphics and other structural graphics could be superimposed to any and all alerts as the personal mobile device moves through various topographies and locales. In addition, any site could show the address, names of individuals involved or security alarm activations at the site if recorded. This dynamic emergency database could be used for emergency responders as well as the general public.

Additional services could be bundled with the mobile safety alert network. These services include, but are not limited to, video emergency tutorials which stream medical survival information, remote triggering application as described in previously in this invention in the form of video and audio, graphs, and other information to a smartphone in order to assist a victim or person in need of medical lifesaving assistance or first aid prior to the ambulance arriving to the scene. Such a service might be exemplified by a medical emergency information application for mobile phones coupled with the personal safety mobile alert system. Thus, one or more synergistic services could be bundled into a single program for a user's mobile device. Described embodiments might allow a user a choice of emergency applications based on an a la carte menu of options and pricing, for example.

For example, applications that provide remote access to a home or commercial security system could be coupled with the personal safety mobile alert system to provide protection of a user's home or business while they are away, in addition to the alert notification system that might offer protection of the individual user. For example, when an individual leaves his/her home, the program could automatically arm the security system and if the security system is breached, an alert could be sent to individuals who live in the same neighborhood through the personal safety mobile alert system showing the location of the home, the time of and nature of the security breach, and the status of emergency responders. This might provide neighbors and authorities the information needed to prevent a chain of related burglaries from happening. The alert might be sent to individuals whose homes/businesses are located within a predetermined area surrounding the location of the security system that was breached. These individuals do not necessarily need to be physically within the alert area, but they will receive the alert as long as their home/business is within that area.

For example, in one embodiment, if a burglar breaks in to "house A" while the owner is across town, the owner receives an alert on their mobile device via the personal safety mobile alert system. If there are 20 houses in the neighborhood, the 20 homeowners might also receive alerts because they have provided their addresses when they first activated and set up the personal safety mobile alert system program. The ability to couple various compatible services creates a broader scope of protection to users. In addition, various historical emergency and crime databases could be streamed to the mobile device and transfer relevant information in real time when passing through various geographies as described in FIG. 11.

Figure 12:
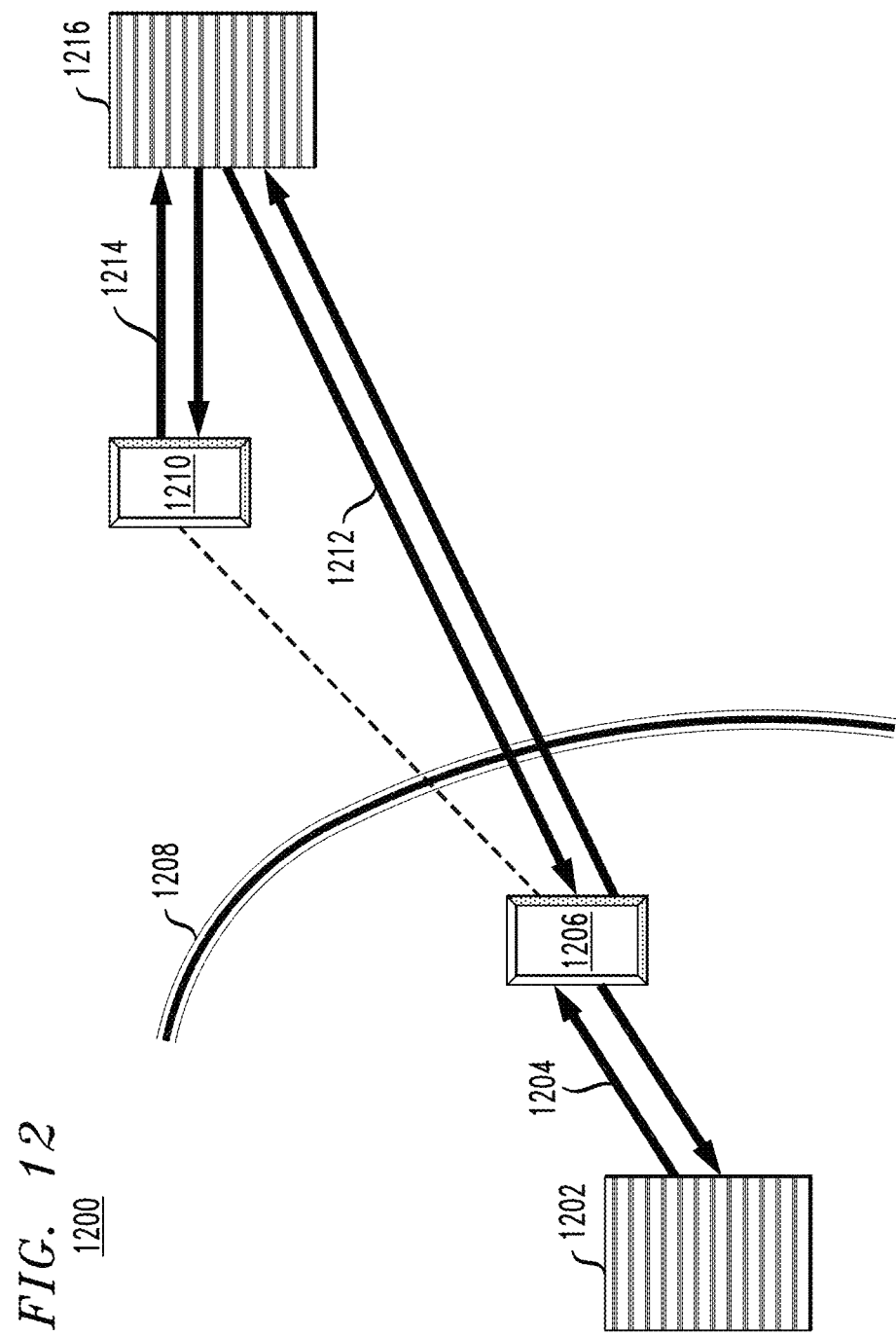
FIG. 12 shows an exemplary diagram of the interconnectivity and communications between mobile-to-mobile devices and server-to-server communications, in accordance with embodiments of the present invention.

FIG. 12 is a representation of server communication to a mobile device in relation to a public mobile communication network and a customized mobile communication network. When mobile device 1210 is outside of a predetermined X-Y coordinates of a customized mobile communication network 1208, the mobile device is in constant two-way communication with the Public mobile communication network servers 1216, as indicated by two-way arrows 1214. When mobile device 1206 crosses over the predetermined X-Y coordinates of the customized mobile communication network 1208, the mobile device 1206 will stay in constant two-way communication with the public mobile communication network servers 1216 (indicated by two-way arrows 1212) while seamlessly establishing a two-way communication with the customized mobile communication network server 1202 (indicated by two-way arrows 1204). Thus, mobile device 1206 is configured to always receive data from the public mobile communication network servers 1216 while receiving customized data from the customized mobile communication network server 1202 only when mobile device 1206 is within the predetermined X-Y coordinates of customized mobile communication network 1208. After leaving X-Y coordinates 1208, mobile device 1206 will no longer have access to or receive data from customized mobile communication network server 1202.

Figure 13:
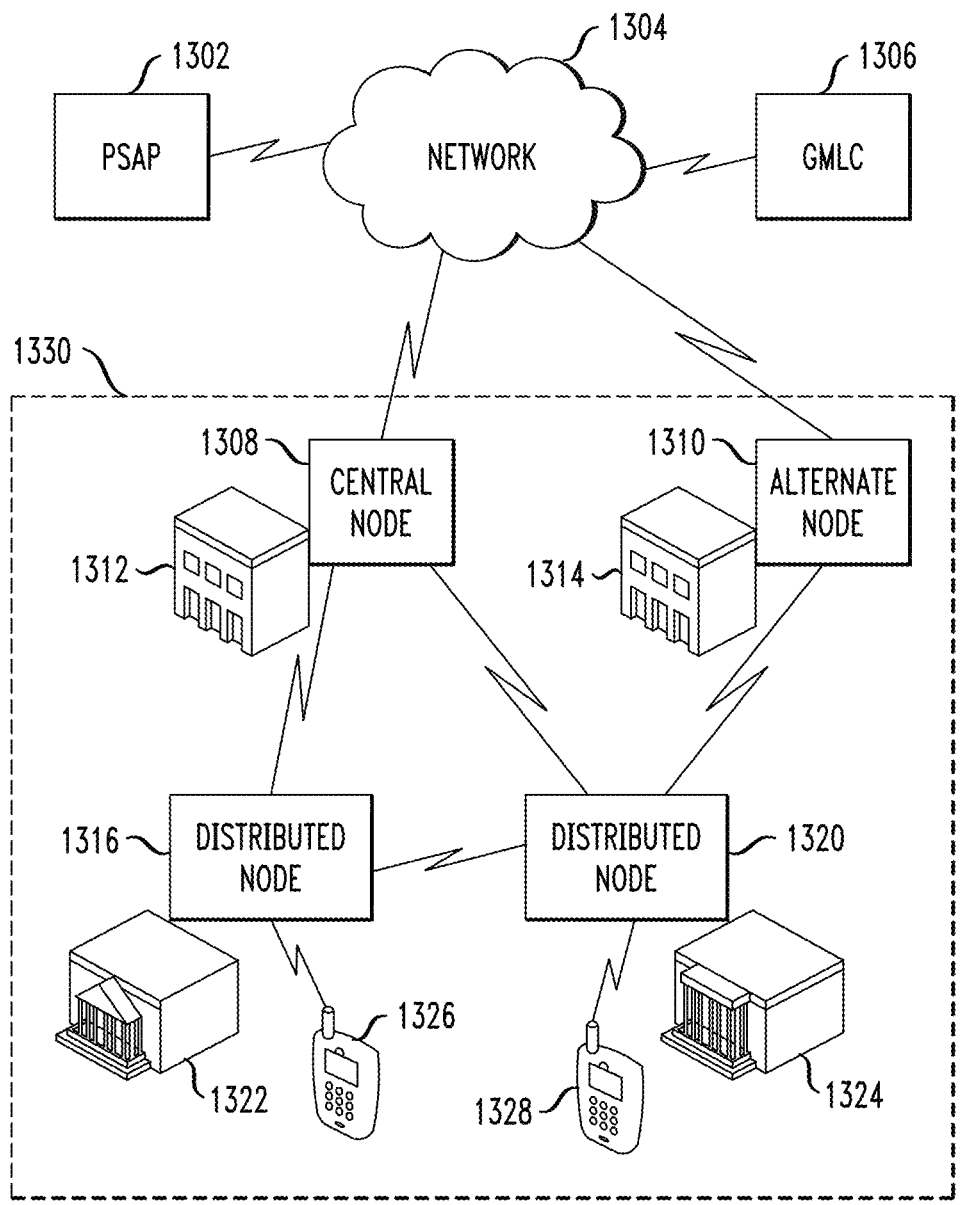
FIG. 13 shows a diagram of an exemplary network and system that may be used to implement a personal safety mobile alert system services using distributed nodes.

FIG. 13 illustrates an exemplary network and system that may be used to implement a personal safety mobile alert system services using distributed nodes. Network 1304 might be any type of network capable of providing wireless services to wireless devices of any type, such as mobile phones. Network 1304 represents any number of interconnected networks that may be composed of any number and type of wired and/or wireless network devices. Network 1304 might provide wireless service to one or more devices within the area of campus 1330. As described herein, campus 1330 might be a school, university, corporate or other campus, or an any area having one or more related buildings shown as 1312, 1314, 1322, and 1324. The buildings of campus 1330 need not be geographically proximate to one another, but might be communicatively coupled through wireless and wired communication networks. As shown, network 1304 might be in communication with a distributed network within campus 1330.

In such a configuration, a central node might be installed on campus 1330, for example shown as central node 1308 installed at building 1312. Central node 1308 might communicate directly with network 1304 and one or more distributed nodes located throughout campus 1330, shown as distributed nodes 1310, 1316 and 1320. In some embodiments, central node 1308 might be a full wireless network base station that directly receives wireless communications data (e.g., data, voice, and any other form of wired or wireless communication) between wireless devices and network 1304. Distributed nodes 1310, 1316 and 1320 might communicate with central node 1308, rather than directly with network 1304, by wired or wireless means.

Gateway Mobile Location Center (GMLC) 1306 might be communicatively coupled to and provide location services for network 1304. When a location of a wireless device is needed by network 1304, for example when an emergency alert is generated, network 1304 might request location information for the calling device from GMLC 1306. GMLC 1306 might determine location information by accessing a database and determining location information from related data, such as a cell identifier. In some embodiments, the cell identifier is a Cell Global Identity (CGI). A CGI might be a concatenation or combination of a Location Area Identity (LAI) and a Cell Identity (CI) that uniquely identifies a particular cell in a wireless network. For example, the operator of network 1304 might provide location information and cell identifiers for each of nodes 1308, 1310, 1316 and 1320 to GMLC 1306, which might store such information in a database. This information may include longitude and latitude, an address, and/or any other physical location information. For each location record stored or accessible by GMLC 1306, GMLC 1306 might also store or otherwise have access to public safety answering point (PSAP) data, such as routing data used by network 1304 to direct a call to a correct destination.

In general, as a distributed network, emergency alert data communications might be relayed between any distributed node 1310, 1316 and 1320 and network 1330 by central node 1308. Data between wireless device 1326 might and PSAP 1302 might traverse network 1304, central node 1308, and distributed node 1316. In some embodiments, alternate nodes might be configured on campus 1330 to provide redundancy or duplicate connectivity means between distributed nodes and network 1304. Additionally, distributed nodes might also serve to relay traffic between other distributed nodes and one or more central nodes.

As one of ordinary skill in the art will realize, network 1304 might be implemented as a wireless service, such as Universal Mobile Telephone System (UMTS), Frequency Division Duplexing (FDD) and Time Division Duplexing (TDD), High Speed Packet Data Access (HSPDA), cdma2000 1x Evolution Data Optimized (EVDO), Code Division Multiple Access-2000 (cdma2000 3x), Time Division Synchronous Code Division Multiple Access (TD-SCDMA), Wideband Code Division Multiple Access (WCDMA), Global System for Mobile Communications of Groupe Special Mobile (GSM), General Packet Radio Service (GPRS), Enhanced Data GSM Environment (EDGE), International Mobile Telecommunications-2000 (IMT-2000), Digital Enhanced Cordless Telecommunications (DECT), 4G Services such as Long Term Evolution (LTE), etc., as well as other network services.

[New Material Starts Here] In addition, embodiments of the present invention might be employed to aid in the safety and protection of property. Property could be tangible objects or intangible objects of any value, importance, or personal interest. Intangible or tangible property (referred to hereinafter as "assets") might be monitored and tracked both when stationary or in motion. Monitoring of assets could be conducted through the constant or periodic evaluation of various environmental occurrences or other events that occur outside of a predetermined acceptable range. Occurrences or events that occur outside of this range or are otherwise deemed to be unacceptable could trigger the sending of an alert. One skilled in the art will realize that the monitoring and tracking of assets could be achieved through any number of technologies including, but not limited to, radio frequency identification (RFID) technology, radio tags, optical emitters and the like. In addition, RFID technology might be integrated with a wireless smartphone or other mobile device employing one or more embodiments of the present invention enabling reading of, and interaction with, active and/or passive RFID tags.

In another embodiment of the current invention, the mobile safety network as described by FIG. 11, FIG. 12 and FIG. 13 and other embodiments of the present invention as described by "campus" as shown in FIG. 3 and FIG. 4 could allow the smartphone/mobile device user to designate a specific meeting place and time, track the location of other mobile devices en route to the meeting place, and alert mobile devices to the existence of any undesirable situation within the area(s). FIG. 1 describes an exemplary GPS receiver, w-fi transceiver, Bluetooth® transceiver, memory, processor, power supply and power management, battery, user entry touchscreen, video screen, camera, audio (speaker, headset, earpiece, microphone), USB interface and secure encapsulator). As previously described, Processor 114 might typically include at least a portion of an operating system of mobile device 100, perform signal processing for signals received from or transmitted to transceivers 104, 106, 108 and 110, and generally control operation of other modules of mobile device 100. Processor 114 interfaces with memory 112, which might include one or more memories for storage of, for example, the operating system of mobile device 100, software applications installed on mobile device 100, various user data such as contact information, calendar information, text messages, email messages, photographs, videos, or other electronic files, messages, or transmissions.

In addition, a smartphone operating in accordance with embodiments of the present invention might interface one or more other mobile devices within a system comprising RFID readers, RF tags, and environmental sensors. Although RFID technology is specifically referred to herein, one skilled in the art might employ other systems or technologies capable of achieving the same functionality. In this particular example, RFID tag and/or sensor information is sent to a reader and the reader could write information back to the RFID tag and/or report the information to the PLMN and/or MSM system and/or mobile devices, peripheral devices, or other devices capable of accepting and/or transmitting data. A mobile device antenna or other transceiver could be used to connect to a wireless network. The device could also possess the ability to directly or indirectly with an RFID reader or device controlling the RFID reader. A smartphone or other mobile device when interfaced, equipped or otherwise integrated with an RFID reader could collect data from various RFID tags, connect to wireless networks and send and receive information across those networks related to the tags, environmental sensors, encapsulators, security systems, and any other information. For example, smartphone technology could be integrated with RFID tags, tag readers, and sensors which could monitor changes in the environment such as climate, motion, and vibration. Mobile devices and smart phones could be equipped with the ability to read and interact with RFID tags at any distance, however several mobile devices could also be integrated or networked together in communication and in some cases a mobile device within said network could remain within a designated proximity of the RFID tags to eliminate the need for mobile devices to remotely interact constantly thus saving battery power, network bandwidth, and other resources.

In another embodiment of the current invention, intangible assets such as digital intellectual property could be monitored and tracked virtually either on the internet, a private network, or a public network to ensure against corruption of data, unauthorized use, unauthorized access, and unauthorized distribution. In other words, digital intellectual property or any art asset could be protected in the same manner described in parent U.S. patent application Ser. No. 12/011,577 filed Jan. 28, 2008. As shown in FIG. 1, mobile device 100 also includes secure encapsulator 130. Encapsulator 130 might transmit real-time information regarding aspects of the asset, such as video, pictures, text and other information regarding the asset. The asset could be monitored and tracked to ensure against the escalation of any undesirable event, status, or state of being (e.g., theft, damage by fire or environmental conditions, and unauthorized movement). Secure cloud networks could be used to disseminate environmental alerts endangering a tangible or intangible asset or person when emergency takes place.

Any conceivable tangible or intangible item of any value might be monitored, tracked, and thereby protected by the current invention. Monitoring, tracking, and reporting on the safety of the assets could be achieved in a number of ways including but not limited to: inventory/asset management software, active and passive RFID technology, RFD readers, NFC enabled devices, distributable nodes, environmental condition sensors, forensic data, global positioning technology, wireless transceivers, cellular transceivers, mobile devices, peripheral devices operating in accordance with the 802.15 communication standard or other wireless standards, the PLMN and MSM as described herein.

RFID is an auto identification technology where a physical object is associated with a unique identifying number (UID) that incorporated in an RFID transponder, or tag. The RFID system has three primary components: a transceiver with a RFID decoder, an antenna or coil and a RFID tag programmed with the UID. In another embodiment of the present invention, asset protection could integrate any form of API, web based or otherwise with the asset. Smartphones or other mobile devices as described herein and equipped with RFID readers could be defined as a gateway between a tag and an intelligent distributed database system connected to enterprise and commercial software applications and other mobile devices.

Identification data could be transmitted using RF frequencies to the RFID enabled smartphone or mobile device which could then transmit said data over the GPRS, GSM, or other phone network and on to a networked centralized management system. The data could be gathered within open or closed loop systems, transferred to public or private networks, stored by one or more centralized databases, or any combination of the above.

Received RFID tag data could be transmitted either over a serial port or a network interface to a corporate enterprise system server or other servers. In addition, the current invention could include various safeguards allowing individuals or organizations secure access to current or past data, reporting, and other valuable information regarding the asset(s) such as history, ownership, title, financial, insurance, location, alert history, current alerts and the status of the resolution of a pending undesirable situation. Note that a redundant system could also be implemented to increase the efficiency of the network of devices involved in the current invention. A user might also access information regarding their own assets or regarding information concerning the assets. The alerts could in some embodiments transfer text, audio, video and or multimedia information related to the asset, the environment, or the status and resolution process of a pending undesirable situation.

Assets protected, monitored, and tracked by the current invention could include any tangible or intangible material item such as, but not limited to paintings, classic cars, coins, stamps, autographs, books, manuscripts, fine art and photographs, films, recordings, compositions, musical instruments, electronics, museum pieces, antiques, memorabilia, patents and intellectual property (IP), music distribution rights, film distribution rights, web content, digital information or artwork, copyright protected IP, confidential documents, or any other privately and/or publically held asset and/or government owned asset. Tangible or intangible assets might be located, stored and/or displayed in one or more countries, and one or more locations such as homes, museums, office buildings, banks, bank vaults, safe deposit boxes, commercial centers, galleries, industrial centers, park and recreation geographies or any other location. In addition, the asset could be tracked when in transit between one or more locations.

The RFID reader might be integrated with the smartphone components such as those described above with respect to FIG. 1. In terms of hardware, the RFID reader IC and the RF antenna desirably fits within a standard handheld mobile device or smartphone. The RFID enabled mobile device or smartphone could include software (e.g., an application or "APP") that programs and/or reprograms RFID tags. In addition, the software could be enabled to both reading from the RFID tags and writing to the RFID tags.

There are four frequency bands for RFID communication varying from low Frequency, high-frequency, ultra-high frequency and microwave. The appropriate frequency for the RFID-enabled smartphone depends on the range required by the application for which it is going to be used. High-frequency bands that allow communication in a few meters are expected to be appropriate for the RFID enabled smartphone. More specify the appropriate frequency ranges in different parts of the globe causing incompatibility issues between tags and RFID readers. The current invention enables RFID equipped smartphones to interface multiple standards, protocols and platforms.

For example, one application might allow a museum patron of the arts to interface in a museum guide of assets through the smartphone device. The smartphone device could provide an interactive asset map of all exhibits within the complex. A virtual tour or exhibit could be customized in accordance to the patron's interest and accessed through their mobile device.

Figure 14A:
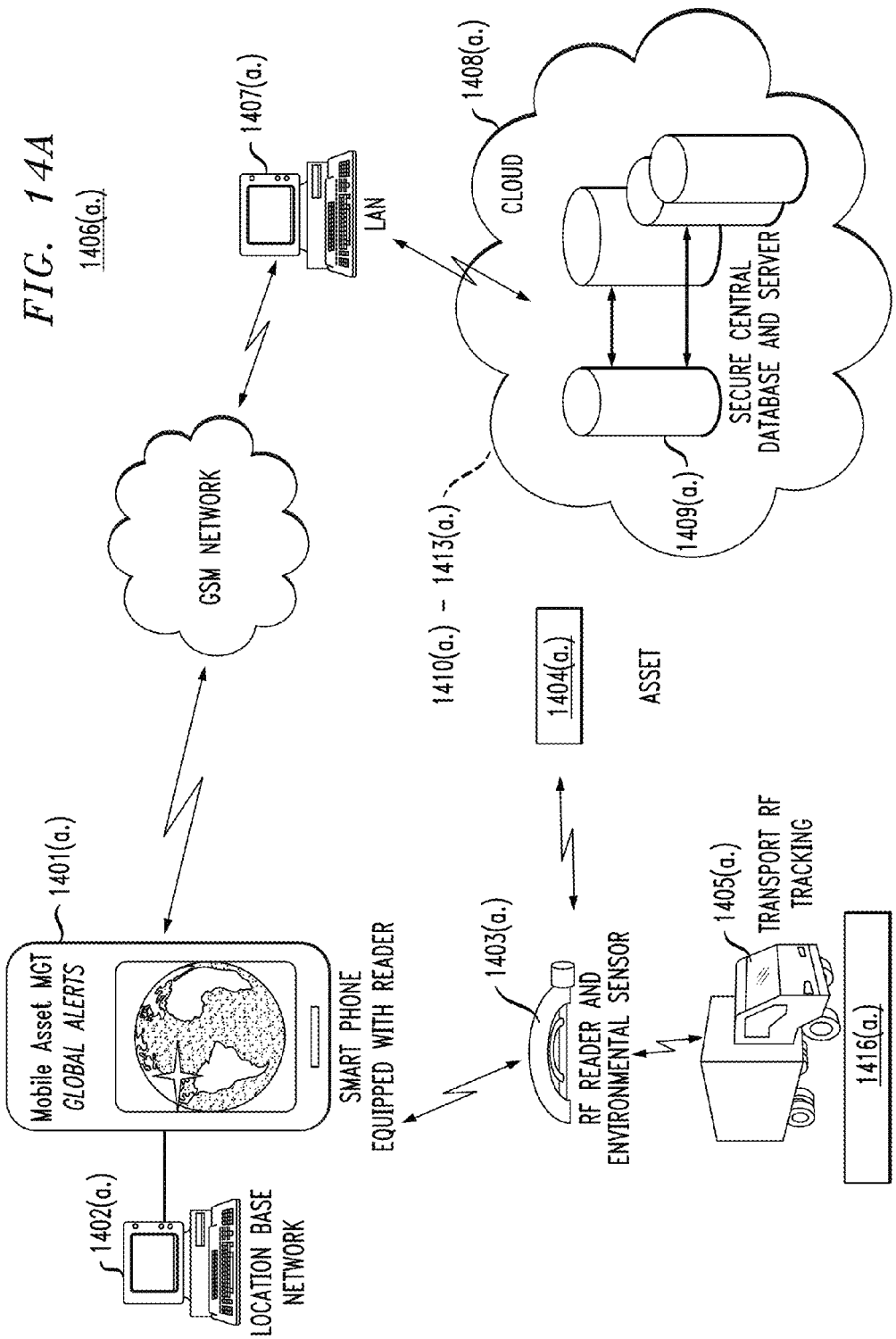
FIG. 14A and FIG. 14B show aspects of an exemplary network database and system that may be used with RFID asset monitoring sensors and smartphone equipped readers.
Figure 14B:
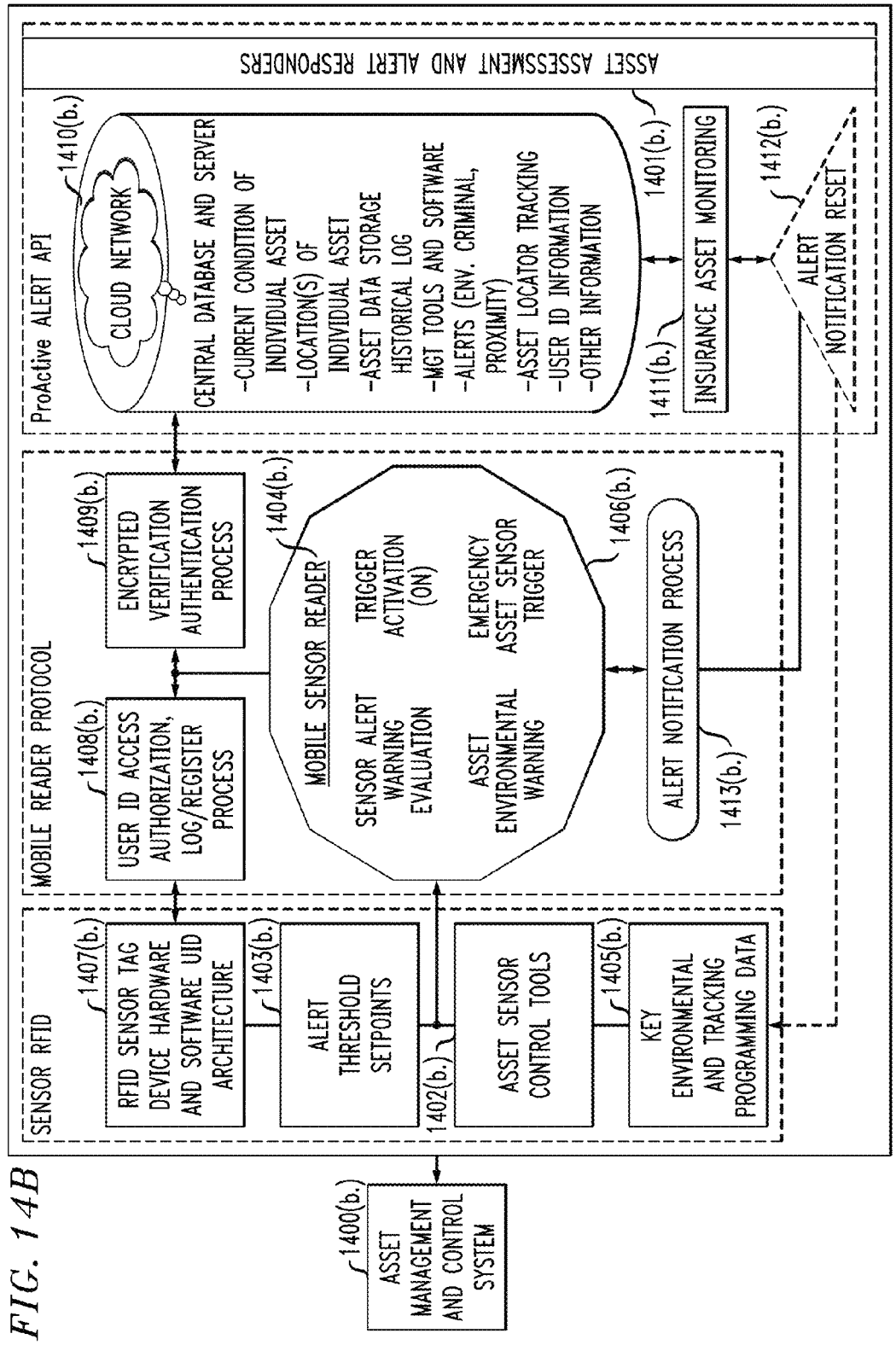

FIG. 14A and FIG. 14B show aspects of an exemplary network database and system that may be used with RFID asset monitoring sensors and smartphone equipped readers. FIG. 14A shows a RFID network 1406 (a.) including a smartphone RFID equipped reader 1401 (a.) which could read one or more RFID sensor tags 1403 (a.). The sensor tag might enable various asset environmental monitoring as described subsequently with respect to FIG. 15.

A mobile device or smartphone could be described as a device that can connect to CPRS, GSM or other wireless networks and is able to run on its operating system an application/software and GUI for the purposes of RFID reading, tracking, and monitoring. It is obvious to anyone familiar with the art that accessory or peripheral RF tag reading devices could also interface with a smartphone. In addition, FIG. 14A and FIG. 14B an exemplary network database and system which could transfer RFID information to one or more external databases that enable one or more value-added services. In addition, the mobile asset MGT system could include any protocol, platform, format, frequency, database network or system. In addition, it should be easily integrated with call initiation or wireless data transmission so that data collected via the RFID reader can be transmitted over the wireless phone network to a centralized database. It may also require special provisions from the smartphone operating system, to generate alerts related to the sensor RFID tag. The communication between the RFID tags and the RFID enabled smartphone could be encrypted using cryptographic algorithms and authentication. The RFID tag sends identification data using RF frequencies and the RFID enabled cell phone transmits it over the GPRS or GSM and phone network to the the centralized asset management and control system.

Referring to FIG. 14A, smartphone device 1401 (a.) is equipped with one or more RF applications and is RFID-enabled. The equipped smartphone reader is embedded with at least one RF transceiver (eg., WiFi or Bluetooth®), an RFID-reader, and environmental sensor reader(s). RFID-tagged tangible asset 1403 (a.) and 1404 (a.), are integrated with the asset management and control system, central database and server and network architecture, as well as a graphical user interface that could be in the form of a software application or hosted on a web server and accessed by way of the internet. Smartphone device 1401 (a.) includes a graphical user interface that could be used by a user to access the features as outlined in FIG. 14A and FIG. 14B. Information associated with any given asset could be accessed by the general public or in cases in which information regarding some assets is proprietary and thus access would be restricted and/or limited. Assets could be organized and referenced in the database by their unique RFID number and other identifying information that could also be stored directly onto the RFID tag itself.

Environmental occurrences include but limited to temperature, humidity, gaseous content, chemicals, air quality, air pressure, radiation, vibration, exposure to light and other factors which will trigger an alert if the optimum range is exceeded or falls below the thresholds of what is determined or generally considered by experts to be optimal conditions. For example, if the active RFID Sensor monitoring of the asset exceeds 23.89° C. and 75° F. the sensor would trigger an alert.

In FIG. 14N, three logical processing sections are shown for the system illustrated in FIG. 14A: the Sensor RFID processing, the mobile reader protocol processing, and the central database/server processing (shown as ProActive Alert API). The smartphone equipped with an RFID reader 1401 (a.) collects information from active and/or passive RFID tags during Sensor RFID processing and transfers the information to the mobile reader protocol processing. The exemplary communication network as shown in FIG. 14 (a.) and (b.) could interface any platform and architectures as well as a multitude of devices through location Base Network 1402 (a.) or a wireless network (e.g., GSM or WiFi). Referring to FIG. 14B, an RFID reader (interrogator) extracts the UID from the tag as referenced by the UID architecture at Sensor RFID processing 1407 (b.).

In some embodiments, the smartphone includes an RFID tag (hereinafter, a "smartphone/RFID tag") and is a device that can connect to GPRS, GSM or another wireless phone network. In other words, the smartphone has an embedded or attached RFID chip with identification information programmed on it. When the smartphone/RFID tag including the RFID reader (e.g., 1401 (a.) and 1406 (b.)) are within range they can communicate: the RFD tag information is sent to the reader and the reader might write some information back to the smartphone's RFID tag. Cloud storage 1410 (a.) through 1413 (a.) represent at least four distinct organizations which could securely access asset information including, but not limited to, alert notifications of information corresponding to actions based on their ownership and service. Cloud storage 1410 (a.) could represent the individual asset owners, financial companies or investment banks' managed investment vehicles that include the assets, private placement investment vehicles including the assets, all of which could access asset information regarding their property, cloud storage 1411 (a.) could represent a manner for insurance companies to manage, track, and monitor assets they insure or are providing policy quotes for, cloud storage 1412 (a.) might represent emergency organizations and other related fields such as forensic laboratories which could be granted limited access based on the severity of a situation or the needs of any investigations they may conduct. Cloud storage 1413 (a.) could represent public access to information regarding their security if held by a public security vehicle such as a mutual fund for example. One skilled in the art will realize that various levels of security and access as well as scope of access could be restricted and controlled by an asset management and control system as described by the current invention. It is also understood that firewalls could be incorporated in order to help retain the integrity of the safety, security and privacy of each asset and or asset classification or fund.

Cloud storage processing 1411 (b.) represents actions such as by insurance companies and other asset owners monitoring and tracking assets that they have insured, and this might be performed in real-time. Mobile sensor smartphone reader module 1404 (b.) and other LAN networks 1402 (a.) might detect alert warnings, environmental warnings and other information if warranted and authorized as represented by processes 1408 (b.) and 1409 (b.). For example, module 1404 (b.) shows a TRIGGER ACTIVATION (ON) switch which could be activated when and if various environmental thresholds are reached. Threshold set-points could be dynamically programmed through a central server 1410 (b.) local severer where the asset is held represented by location base network 1402 (*a.*) and/or by a smartphone reader equipped device (as shown by 1401 (*a.*) and 1404 (*b.*) and herein described).

Non-wired RFID sensors generally rely on an independent battery power source. The current invention includes periodic and or constant monitoring of the asset. However, periodic monitoring and constant monitoring when not wired to a power source could exhaust battery power. One of the main benefits of the current invention is that threshold set-points and ALERT TRIGGERING extends the life of the RFID battery when armed to protect the asset. Alert threshold set-points 1403 (*b.*) are generally predetermined through industry practice or experiment. A Mobile Sensor Reader module 1404 (*b.*) defines TRIGGER ACTIVATION (ON) as harmful or otherwise unacceptable situation occurring (usually in real-time). This alert activated TRIGGER ACTIVATION (ON) thus minimizes battery consumption by activating full functionality only in the event that undesirable conditions occur outside of the predetermined acceptable optimal limits required to maintain and protect the asset. For example, instead of constant monitoring of temperature, the alert trigger(s) could be engaged if the thermometer crosses a programmed minimum or maximum temperature threshold and/or a humidity set-point, maximum light exposure, or unauthorized movement or proximity. When the set-point threshold is crossed the sensor will activate and signal an alert to an asset management and control system. For example, the RFID sensor threshold set-points 1403 (*b.*) could be programmed to monitor the air for smoke or other gases, chemicals, and airborne substances that could potentially damage the asset. If it were determined that the air quality around the asset had exceeded acceptable levels, this would automatically trigger and set in motion the alert process.

The advantages of the automatic triggering of the alert system include maximizing battery life while minimizing monitoring requirements. In addition, solar powered RFID sensors and other similar green technologies might be used to power RFID and sensor units in order to extend battery life while in transit over long distances:

Key environmental monitoring and tracking data module 1405 (*b.*) receives and processes data that might be entered from one or more databases in order to provide various functional asset sensor control tools (e.g., management/managerial command control) 1402 (.*b*) and set-points (thresholds) 1403. (*b.*). Optimal environmental conditions might vary greatly depending on the classification of an asset. For example, rare coins might not be as susceptible to exposure to sunlight, but rare painting are. One skilled in the art will realize that the alert threshold set-points as well as the types of environmental and other conditions being monitored could vary widely depending on the asset and the situation. In some cases, comprehensive monitoring and tracking measures might be required, while for other cases monitoring and tracking could be handled to a more limited degree. This level of monitoring and tracking might be determined, for example, by an asset owner, experts, managers, or by insurance companies.

The host database and server represented by 1407 (*a.*), 1408 (*a.*), 1410 (*b.*) could store information regarding the asset such as, but not limited to, history of the asset, location, environmental historical archive of alerts, financial information, title and ownership history, market price valuation data, quality evaluation data, forensic history and data, appraisal information and other qualitative and quantitative analysis. Said database and server represented by 1407 (*a.*), 1408 (*a.*), 1410 (*b.*) might also incorporate the features of PLMN and MSM as well as the CCM system as described in U.S. Pat. No. 8,015,069, filed on Nov. 20, 2007, the teachings of which incorporated herein in their entireties by reference.

Access to asset information could be controlled by incorporating a user ID, biometric access and other means of secure login registration via module 1408 (*b.*). In addition, management control system 1400 (*b.*) and central database and server module 1408 (*a.*)/1409 (*a.*)/1410(*b.*) could generate, store, and present real-time and archival data on an individual asset or group of assets, location(s) of the asset(s), information regarding storage and the archival history of placement and other management tools including but limited to location tracking, environmental sensor alerts, theft alerts, alerts concerning important market information regarding the asset(s), and other information regarding the monitoring or history of the asset(s).

In another embodiment of the current invention, alert threshold set-points 1403 (*b.*) based on the acceptable range of conditions might be dynamically adjustable when moving the asset from one approved location to another in order to adjust to altitude, humidity, temperature and other factors. FIG. 14A shows RFID sensor 1403 (*a.*) attached or in proximity of the asset. These sensors could detect any environmental threshold which could affect the tangible or intangible asset. Detector 1416 (*a.*) might be, for example, a motion detector attached to the RFID sensor which could monitor the movement or proximity of a person to the asset as well the proximity of a person getting too close to the asset as exemplified by a person crossing the line and moving too close when viewing a museum art asset. If a person goes over the designated line the motion detector could trigger the sending of an alert notification to museum security guard(s) mobile devices within the area (as represented by alert 1505, described subsequently for FIG. 15).

The programming of set-points for each RFID sensor tag monitoring the asset could be programmed to trigger an alert based on exceeding various environmental set-points (e.g., programmed to trigger warning when environmental conditions warrant). For example, if a temperature set-point optimal storage temperature is 68° F. and elevates to 70° F., given the danger threshold alert was set at 72° F./22.22° C. the warning alert could be sent to the persons responsible for the asset. The programming of set-points for each RFID sensor tag monitoring the asset might also be programmed to dynamically adjust set-point thresholds to meet all unique conditions of place and environment. The programming of set-points for each RFID sensor tag monitoring the asset might further be programmed to trigger an alert based on periodic or constant monitoring of environmental conditions. Constant monitoring could be necessary in certain conditions when transporting the asset for example or after an alert has been activated. When an alert has been activated the environmental sensor could be reset and rearmed (as shown in FIG. 14B by processes 1412 (*b.*) and 1413 (*b.*)). The alert or alert information could be logged and archived in the central database for future reference.

Table 3. Shows an exemplary set of threshold set-points which could be programmed onto the RFID tags themselves via the wireless network or on site. As shown in Table 3, a temperature set-point, for example, for a Van Gough painting represented by the RFID tag serial number/UID number (as referenced in FIGS. 14B and 15 as 1407 (*b.*) and 1504) could, for example, refer to the specific asset 1774087481245490189. Asset serial number 1774087481245490189 has, for example, an optimal temperature range of 68° F.-72° F. (20-22.22° C.), if a temperature over 72° F. (22.22° C.) is reached an alert could be sent out to all parties associated with the asset. In addition, Table 3 exemplifies other environmental condition set-points such as humidity and lumens. One skilled in the art would might extend the teachings herein to set other condition and environmental set-points, which are then programmed and monitored.

TABLE 3

ENVIRONMENTAL RFID SENSOR THRESHOLDS SETPOINTS

| Form of Asset/ Material | Relative humidity in % | Temperature in °C./FH | Illuminance in Lux |
|---|---|---|---|
| 1. Optimum Painting Setpoint | | | |
| RFID No. 177408748124549018 Van Gough 2. Oil and Acrylic | 45-50 | +20-22.22/68-72 | Varies, stability is best for all |
| Paintings on wood or canvas | 50-65 | +20-23.89/68-75 | 150-200 max. 500 short term |

FIG. 15 shows a smartphone equipped with a reader screen display (mobile device 1500) exemplifying various real-time and archival sensor data from one or more RFID sensor devices. Mobile device 1500 as described by FIG. 15 is equipped with a sensor reader reads tags and is alerted if the RFID Tag reader and/or sensor monitoring the asset detects an environmental condition that falls outside of an acceptable range of measurements or threshold set-points (thus triggering an alert). Optimal threshold set-points could be defined as a measure of temperature or a maximum relative humidity percentage, the detection a vibration which exceeds an acceptable m/s$^2$, light exposure which exceeds an acceptable level of lumens, static electricity exceeding beyond a acceptable kv unit, and other environmental conditions which could affect the value and longevity of an asset. In addition, smoke detection, motion detection and a multitude of other environmental sensors set-points could be monitored by the current invention as represented by 1503.

RFID Alert data 1504 as shown might include information of standards established by the Electronic Product Code (EPC) and International Organization for Standards (ISO), which define data structures within the tag and allowed/available frequencies. One skilled in the art will recognize that the current invention might utilize any frequency, standard or platform available for such purposes described herein. RFID numbers could include a comprehensive database of information pertaining to one asset or a group of assets.

Smartphone equipped readers could access global sensor alerts resulting from environmental triggers, as referenced by various entries 1503. A central computer system could log, trace and monitor one or a multitude of various asset classifications, located in various geographies and stored under a wide variety of conditions and programmed setpoint thresholds. Each art asset and corresponding RFID tag could be globally monitored by authorized personnel order to protect the asset.

The RFID tag could contain information regarding history of the asset, ownership history, financial data, present location, past locations, location tracking, asset security, environmental climate security and other information regarding the asset. Sensor alerts 1503 reference various environmental sensor alerts from one or more location. Environmental sensors as exemplified by alerts 1503 represent built-in sensors including but limited to temperature monitoring alerts, light exposure monitoring alerts, humidity alerts, air composition alerts, chemical alerts, vibration alerts, weather alerts and the like. A comprehensive Geographical Information System (GIS) 1506 could integrate with the asset management and control system, PLMN, and MSM alert systems to track and monitor assets as well as capture, store, manipulate, analyze, manage, and present all types of geographical data information as shown in the Mobile Asset Management Reader icon represented by FIG. 15. The alert information could be accessed through one or more secure networks or central servers as previously described.

In addition, the host computer as well as mobile devices equipped with readers could securely access and receive information and alerts from one or more locations. For example, temperature sensor alerts 1501 (and 1601 of FIG. 16 described subsequently) reference six alerts related to assets in different locations that exceed the optional range of 72° F./22.22° C. Intangible and tangible assets and property locations could be vaulted, in a home, commercial building, displayed in a museum or gallery or any other outdoor or indoor environment.

If the RFID system detects a problem with the asset, an alert could be sent to various smartphones and closed end or opened ended databases or sub-databases. Information pertaining to a single RFID monitored asset could for example, provide text and or audio, and or visual and or multimedia commentary of the art asset through the smartphone or other device.

The application could be capable of utilizing WiFi or WiMax communication, or communication via other wireless frequencies, and access a wireless router in order to disseminate any and all information regarding one or more assets within a given geographic location or a multitude of locations. It must also be noted that the coordinates of an asset could be determined according to not only the "x" and "y" values but the "z" indicating altitude as well.

Theft alerts as represented by alert 1507 are based on the theft of any asset of any value tangible or intangible. The alert process might be as described in U.S. Pat. No. 8,013,734, filed on Jan. 28, 2008, and US Patent Application Publication No. 20110130112, filed on Feb. 7, 2011, the teachings of both of which are incorporated herein in their entireties by reference. The alert process might include the addition of RFID sensors monitoring the theft of the asset as previous described in the context of the asset based sensor alert management system.

Alerts 1502 (a.) represent various GPS asset tracking alerts, which in the example shows 8 assets in different locations that are accessed through the Mobile Asset Management System through one or more servers and subservers. In addition, Locator 1502 (b.) refers to a locator GPS Beacon for each transit alert which logs and stores the position and trail of the asset within the transporting vehicle at regular intervals.

Figure 16:
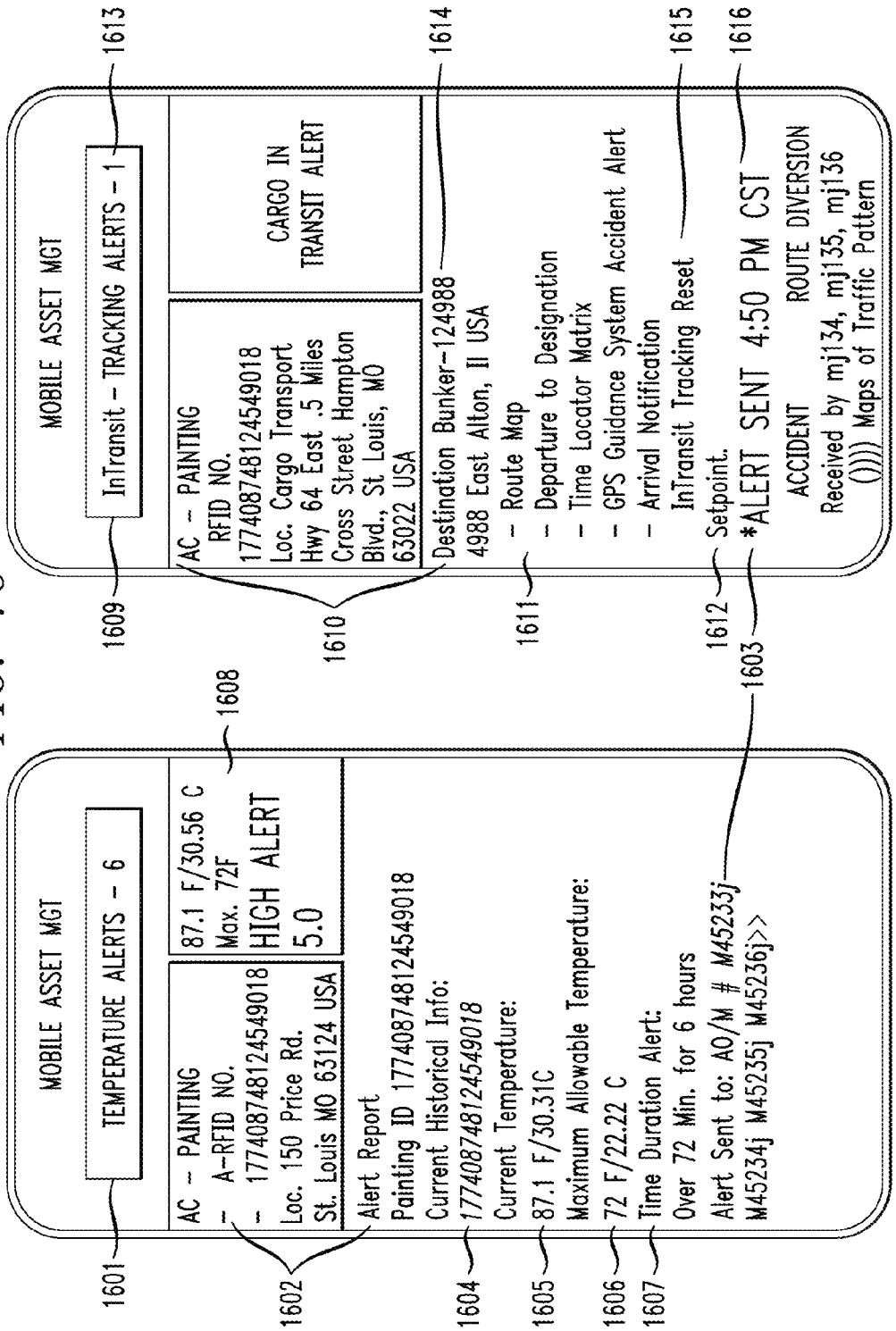
FIG. 16 shows an exemplary smartphone equipped with a reader screen display exemplifying an alert based on temperature monitoring and asset tracking.

FIG. 16 shows an exemplary smartphone equipped with a reader screen display exemplifying an alert based on temperature monitoring and asset tracking. Alerts triggered by an unacceptable change in temperature are a component of the environmental threshold set-point as shown by alert 1601. Alert 1601 shows six global alerts that were sent to the owner(s) of the assets or organizations involved with the assets. Address data 1602 shows the location address of one of the exemplified alerts. RFID number: 177408748124549018, in this example, is located at 150 Price Rd. S. Louis Mo., 63124, USA. Also, detailed current and historical information regarding the asset(s) and related or unrelated to alerts could be accessed. RFID serial number 1604 could be cross referenced to the specification of the temperature alert 1605 which posts a current temperature of 87.1° F./30.31° C. and which could be updated regularly in real-time. Maximum allowable temperature 1606 exemplifies the maximum allowable temperature programmed through the threshold set-point parameters. Time duration alert 1607 shows an example of the time duration of the alert from the time it was initiated up to the present time. The time could be translated to any standard time zone, date and time scale. Alert 1603 refers to a "Mobile Asset Network" alert sent to Asset Owners and Managers (AO/M's) exemplified by M45233j and other mobile shared mobile access codes. Alert scale 1608 quantifies a dynamic analysis management tool that is capable of prioritizing incoming alerts according to their urgency and state of resolution.

In Transit tracking alerts 1609 references an example of an alert in which an asset is being tracked and lists the number of managed InTransit alerts (which in this particular example is one). Screen area includes data 1610 that identifies the RFID number and current location of the asset in transit. A map 1611 could be used to display the location of the asset, the destination, structures that are being entered or exited, a time locator matrix, GPS guidance system accident alert, arrival notification and in-transit tracking set-point and reset-points as described in FIG. 14B, as well as the optimal approved route. 124988 referenced by data 1614, represents a serial number for a designated destination. Data 1615 references the time the alert was sent. Data 1612 exemplifies an accident and a route detour in order to avoid weather conditions, road construction, reported theft alerts and other hazardous conditions which could otherwise jeopardize the safety of the assets. In addition, it is obvious to anyone familiar with the art that other information could accompany the InTransit alert, such as but not limited to traffic patterns, maps and other environmental conditions.

Figure 17:
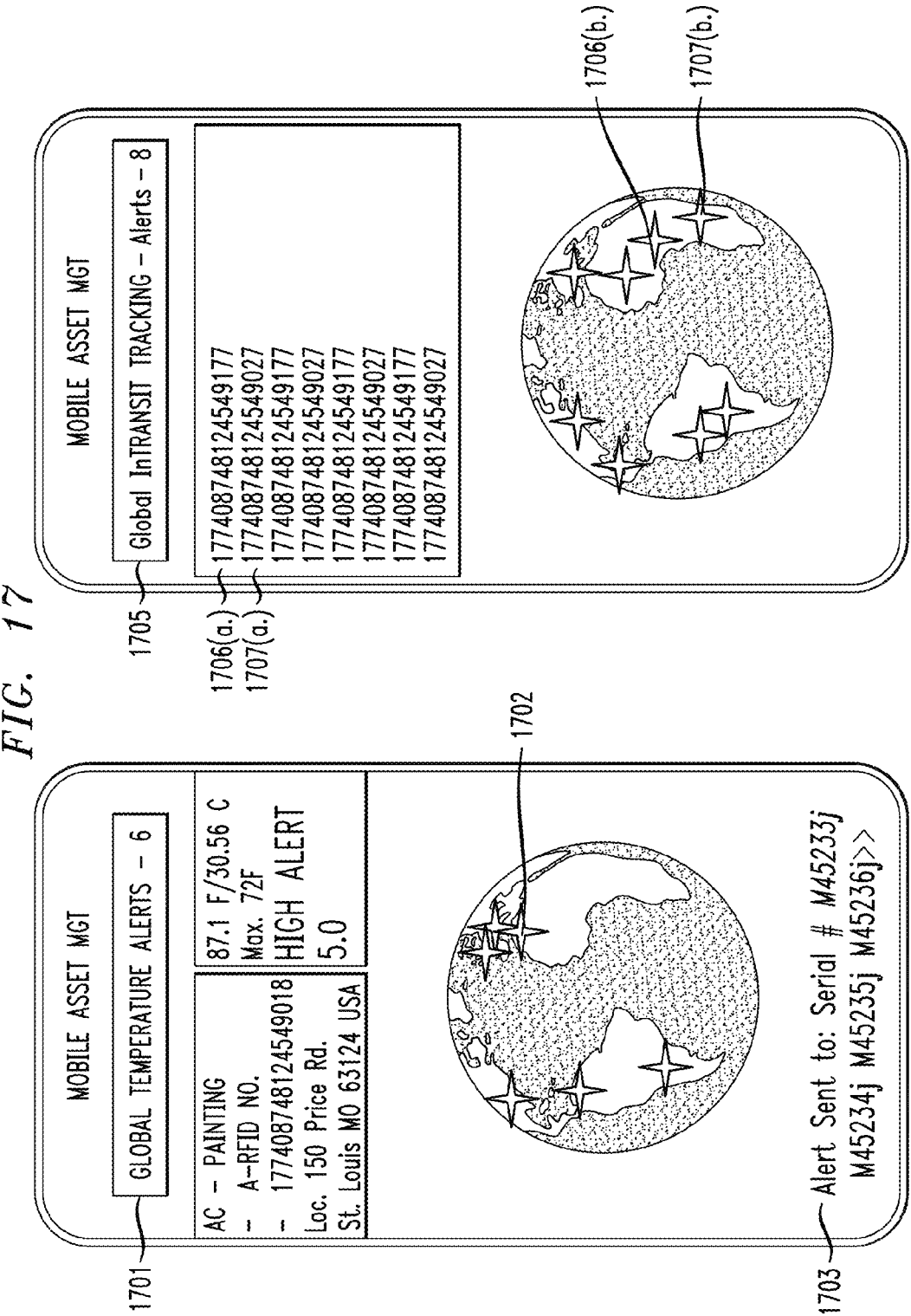
FIG. 17 shows an exemplary smartphone equipped with a reader screen display with intraoperative global information systems tracking global assets and alerts.

FIG. 17 shows an exemplary smartphone equipped with a reader screen display with intraoperative global information systems tracking global assets and alerts. Temperature alerts detected globally total six in example. Map display area 1702 enables the user to pinpoint one or more assets which a temperature alert has been detected and through the touch screen zero in on the precise GPS location. In addition, other information regarding the temperature and other related sensor activity could be viewed in real-time. Archival alerts for asset shown on map display area 1702 could be accessed as described previously in the current invention. Mobile InTransit alerts tracking alert globally total 8 in this example as shown in alerts 1706 (*a.*) and 1706 (*b.*). The RFID serial number might be accessed in order to check transit status, cargo authorization, vehicle registration, transit route, third party transportation companies and organizations, driver's licenses, weather and other conditions, road construction, purpose of shipment, value, information about the asset and it history, ownership and other information.

A Mobile Asset Management network might give users the ability to keep track of a vehicle charged with transporting an asset as well as the individual asset itself. The system in some embodiments of the current invention, might link the assets RFID to the vehicle's RFID through a PID data pusher or other data archetypes. GPS or other similar technologies could be used for asset tracking, personal tracking, vehicle tracking and other related tracking requirements relative to the global tracking of assets 1706 (*b.*) and 1707 (*b.*) that are classified as in transit.

Figure 18:
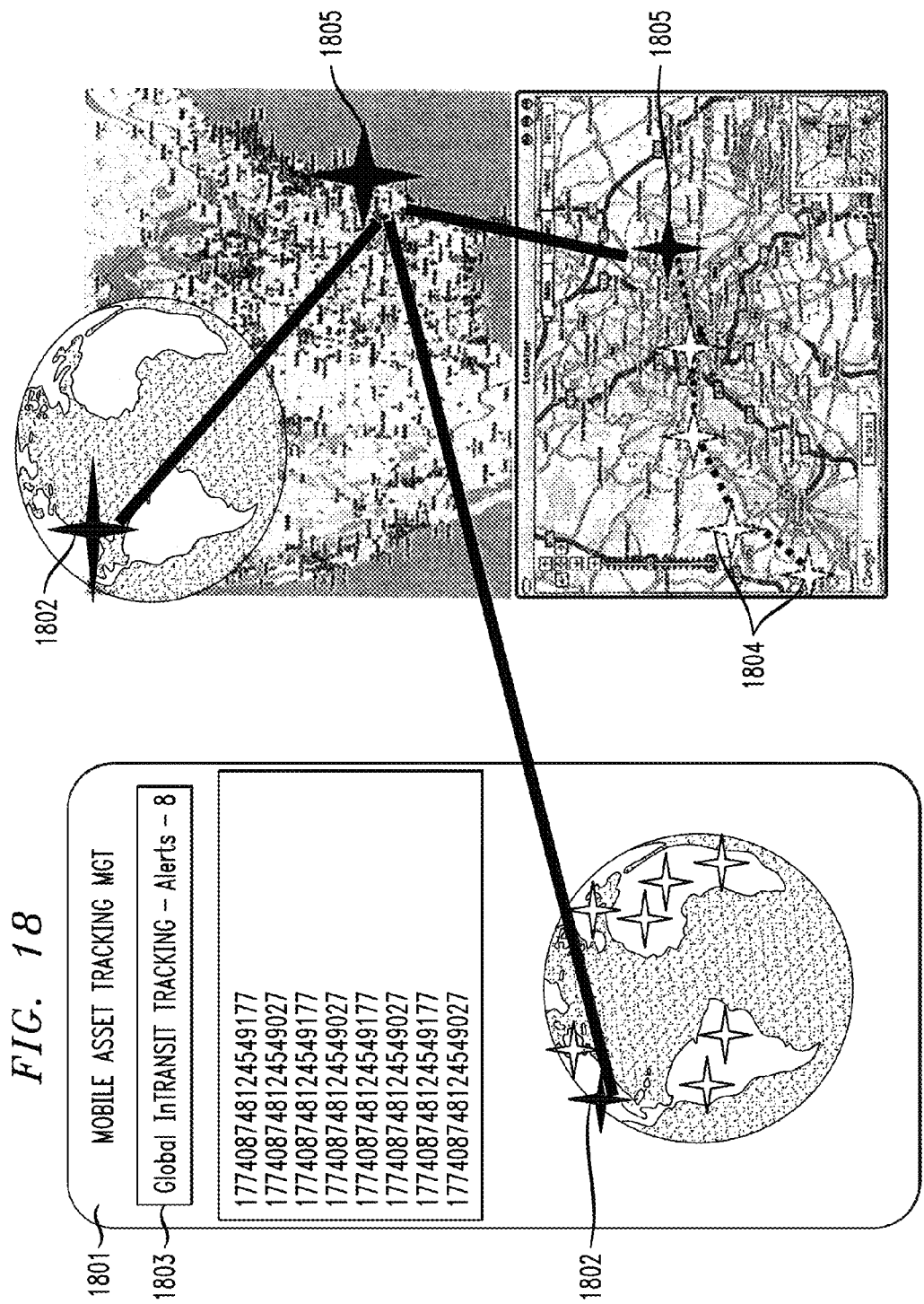
FIG. 18 shows an exemplary tracking system of assets when being transported from pickup through delivery.

FIG. 18 shows an exemplary tracking system of assets when being transported in conjunction with a network of mobile devices and alert notification based on weather and traffic conditions from the pickup location through delivery. A GPS logger could record the in transit (InTransit) positions of one or more asset as shown at display 1801 at regular intervals in its internal memory within the RFID chip and or mobile reader. Display portion 1803 shows eight InTransit alerts having been logged and tracked through GPS from the original starting point exemplified by displayed global position 1802. A memory card slot, or internal flash memory and a USB port could be interface the mobile device allowing downloading of the track log data for further analysis from the cloud network through the mobile asset tracking and management system. In addition, various tracking technologies could be used including but not limited to GPX, KML, NMEA or other format.

A GPS navigation device and GPS-integrated mobile devices or smartphones running GPS tracking software might enable the device to be a data pusher (or logger) device. "Bread crumb" GPS asset tracking exemplified by transit path display 1804 might track the transported asset from its original designation. Point-to-point access to the InTransit cargo could be achieved by a combination location hardware (or tracking devices) and tracking software. This combination is often referred to as an Automatic Vehicle Location system. The tracking device might be hardwired and installed in the vehicle; connected to the CAN-bus, Ignition system switch, battery. It allows collection of extra data, which could be transferred to the GPS tracking server and available for viewing via a secure website accessed over the internet, where asset tracking can be viewed live or digital maps and reports to its final designation as exemplified by endpoint 1805 might be stored and referenced at any time.

GPS data pullers, also known as GPS transponders, might be incorporated to track the position of assets position at regular intervals; these devices are "always-on" and might be queried as often as required. GPS data pullers can often be used in the case where the location of the tracker will only need to be known occasionally e.g. placed in area with high risk of a theft alert, or that does not have constant supply of power available therefore limiting the ability to send data on a constant basis.

Figure 19:
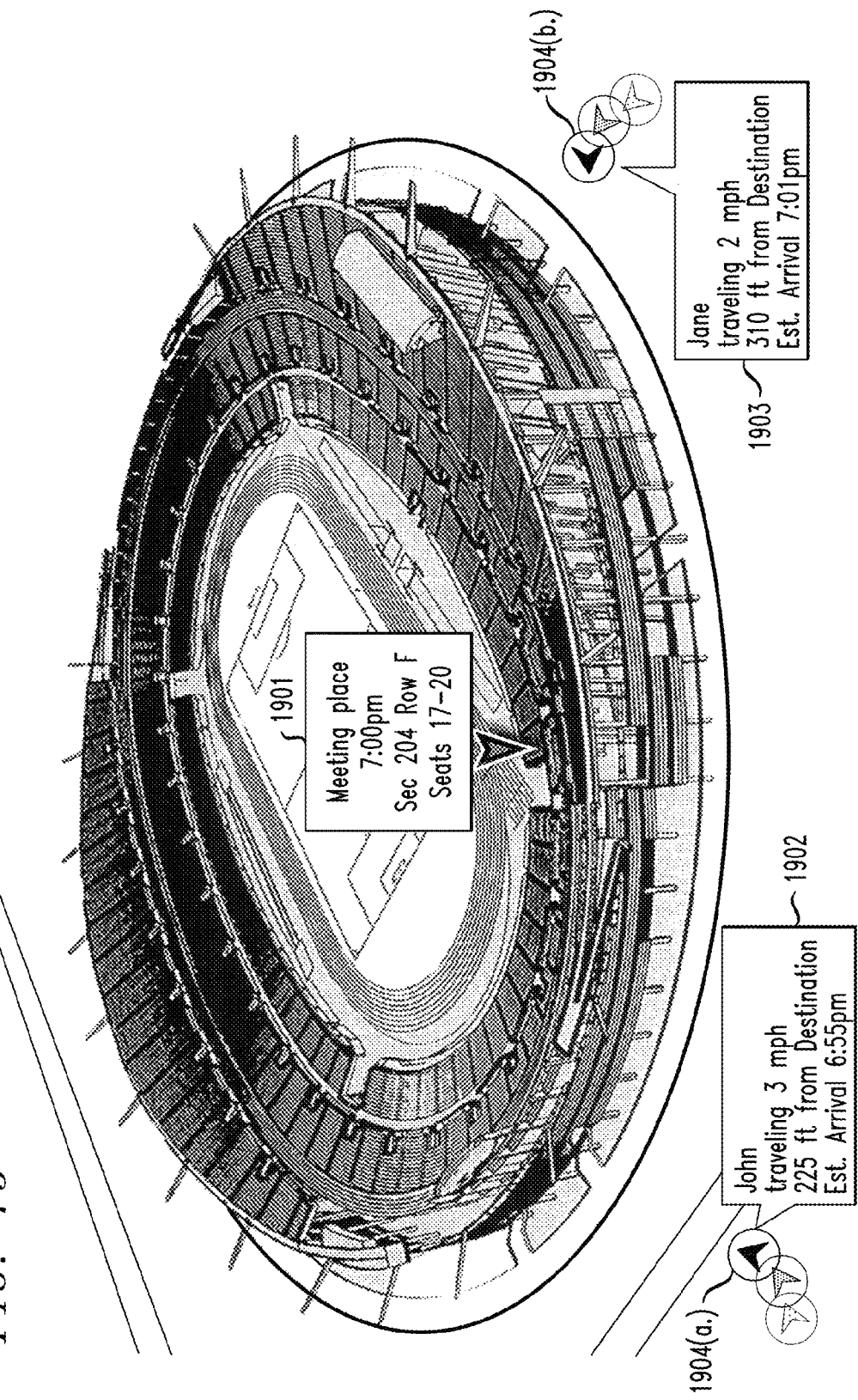
FIG. 19 shows an exemplary tracking system of assets in which guest-smartphones are moving toward a site established by a host-smartphone.

FIG. 19 shows an exemplary tracking system of assets in which guest-smartphones are moving toward a designated site established by the host-smartphone. Host-smartphone 1901 establishes a hosted meeting designation including xyz coordinate locator and time. The setting of a campus based environment could include any building and or geography. The "campus" in this example a stadium was entered by the host-smartphone as the meeting place (section 204, Row F, seats 17-20, is shown in FIG. 19 as the designated location). The time established by the host-smartphone is 7:00 PM CST. Guest-smartphone invitees are limitless and could include guests carrying smartphones which travel to the hosted meeting designation by car, foot, boat, plane, train or any other means of transportation. In addition, the smart system could include groups which are in real-time tracked by one or more guest or host-smartphones. In another embodiment of the current invention a GPS logger could log the position of one or more devices and not only track real-time positions, but also the positions of any guest-smartphone or other mobile device as well as access archival information such as positioning, information regarding the event or place, warnings, alerts and other safety information.

GPS pathways 1904 (*a.*) and 1904 (*b.*) illustrate paths taken by two guest-smartphones as logged through respective GPS coordinates. GPS pathway 1904 (*a.*) exemplifies a guest traveling at 3 mph toward the host-smartphone designation. The guest-smartphone (with user named "John") has an estimated time of arrival of 6:55 PM as given in label 1902. Although the user in this example is traveling by foot, it is understood by anyone familiar with the art that any transportation method could be used and displayed as such to users. Another guest-smartphone (with user named Jane) is traveling at 2 mph with an estimated time of arrival of 7:01 PM as given in label 1903.

Figure 20:
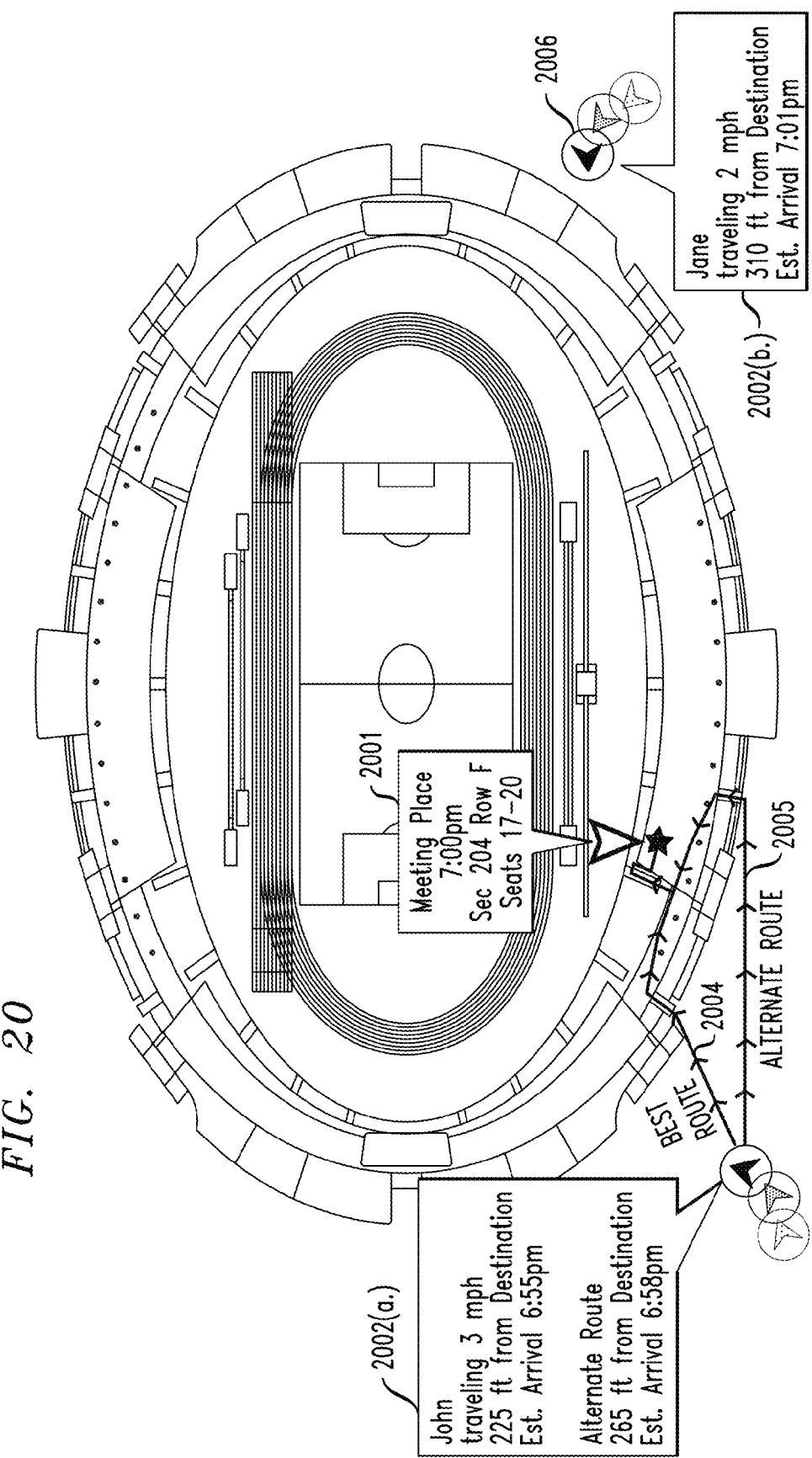
FIG. 20 shows an example of a host-locator campus meeting place and time with two tracked independent guest-smartphone devices.

FIG. 20 shows an example of a host-locator campus meeting place and time as well as two independent guest-smartphone devices being tracked. GPS pathway 2002 (*a.*) illustrates John's path to the host-smartphone's meeting designation. Path 2004 is an example of a "best" path, where "best" is, for example, either a shortest, a fastest, or a safest course of travel to destination 2001. However, in this example John has taken an alternative path which now increased the estimated time of arrival to 6:58 PM. The other user (in this example, named Jane) 2006 along GPS pathway 2002 (*b.*) is provided optimal and alternative route information and is also provided with the other user's (John's) route information and options as well. In another embodiment of the invention, when Jane's guest-smartphone approaches the stadium, a diagram map of the stadium might be displayed on the corresponding smartphone in a manner as a street map if "walking" is displayed. The football game's score, game brochure, concession stand locations, menus and specials, electronic tickets for admission into the stadium and other information might also be embedded on the phone and securely accessed and retrieved. Radio Frequency Identification might be integrated in a combination with other wireless platforms, databases and cellular networks in order to provide seamless access to enriched data. Guest-smartphone users as well as host-smartphone users might access all types of data including, but limited to, text, maps, video, audio or multimedia.

Figure 21:
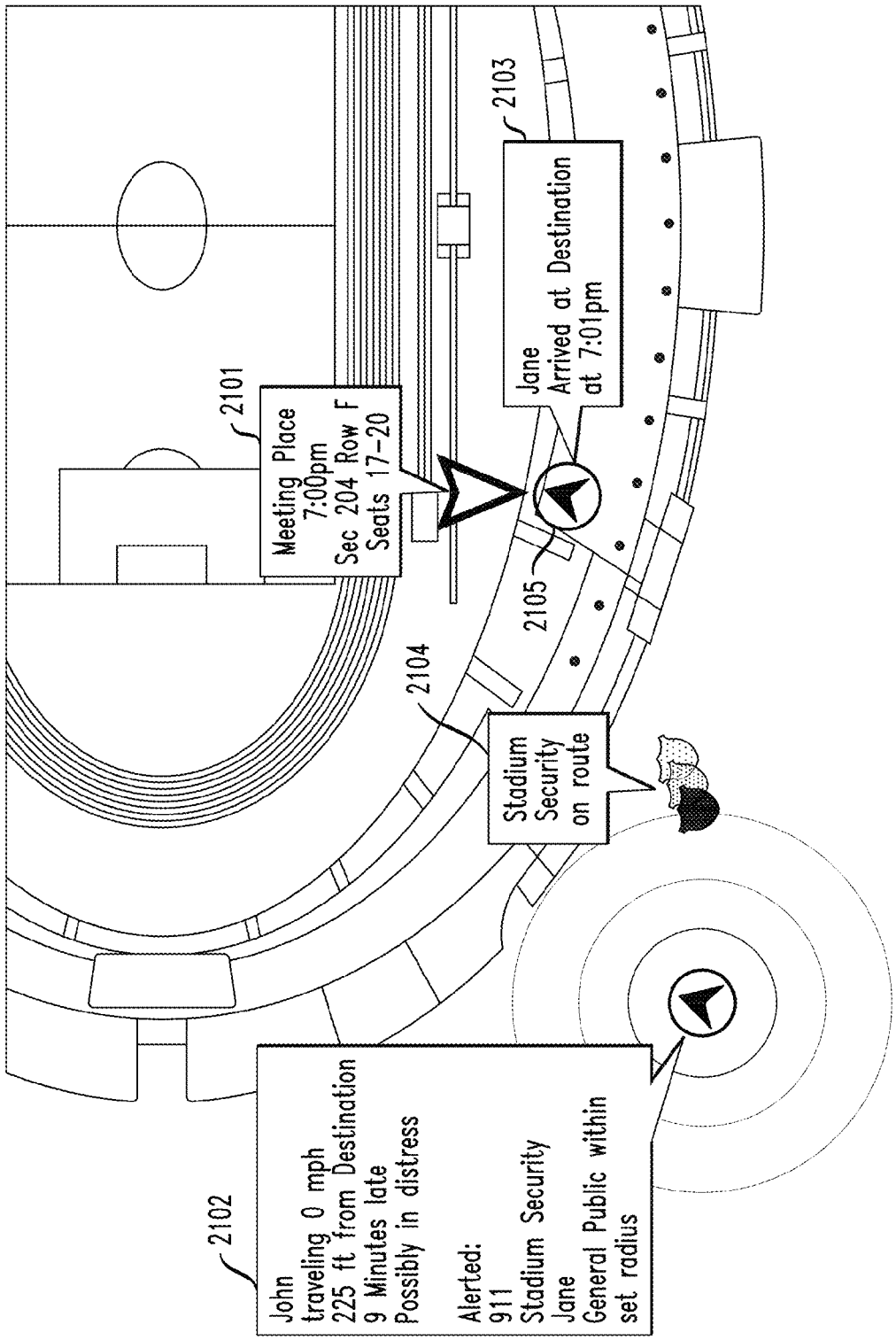
FIG. 21 shows an exemplary host-smartphone alert based on failure of a guest-smartphone arrival to a designated site.

FIG. 21 shows an exemplary host-smartphone alert, based on a failure of the guest-smartphone's arrival to the designated and scheduled-time meeting site. Event 2105 shows an exemplary confirmation that the guest-smartphone 2103 held by Jane has safely arrived at the host-smartphone designated site. Concurrently, the host-smartphone GPS tracking system warns the host that one of the guest-smartphones is nine minutes late and not moving. 2102 shows John's guest-smartphone is travelling at 0 mph and that the MSM system has determined through collecting encapsulator data the possibility that John may be in distress.

The "Mobile Safety Network" could enable the host-smartphone to directly contact the guest-smartphone inquiring if they are in distress or lost and or send a message to the general public within various set radiuses. In addition, as referenced previously in the current invention, one or more host-smartphones could attempt to contact one or more guest-smartphones if a delay in arrival occurs.

For an example an overriding message to the guest-smartphone could send an audio, text, or other message regarding if the user is distressed or in trouble. Overriding, as defined in the present invention, is the ability to remotely to activate the guest-smartphone 2102 based on previous permission from John to allow environmental encapsulator functionality. The ability to activate a cell phone that is turned off or not functioning could be utilized by the 2101 host-smartphone or emergency dispatch authorities 2104 as previously described as embodiments of the current invention. The permission to allow another device to remotely access encapsulate the audio, video, photos, real-time or archival location tracking could be either temporarily granted or controlled by the guest-smartphone. It is obvious that in case that an alert is sent from the host to the emergency dispatch units and or in this example stadium security 2104, emergency authorities could circumvent access any data necessary to assist the individual in need.

Figure 22:
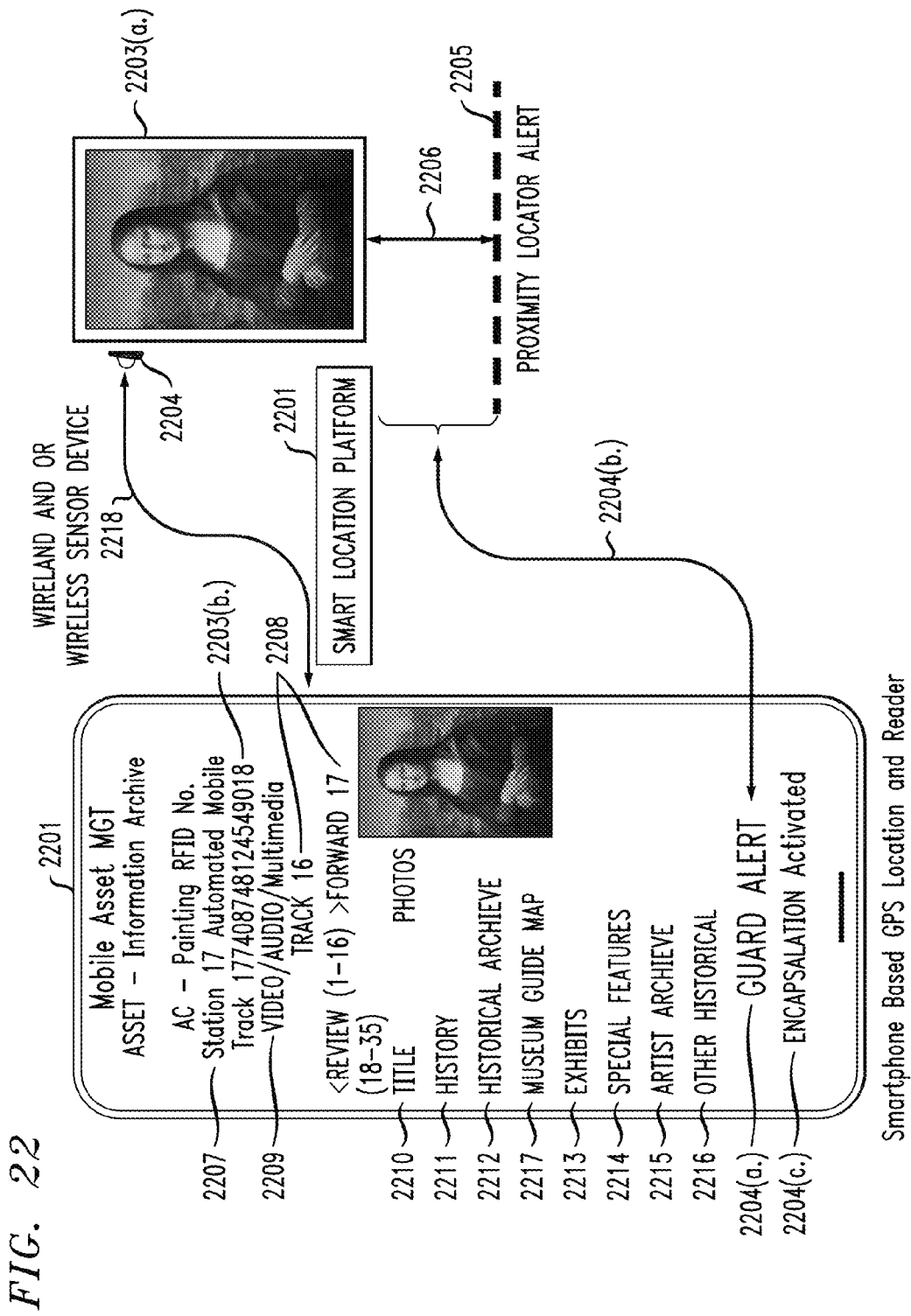
FIG. 22 shows an asset at a location, equipped with an RFID sensor/tag and in communication with a smartphone operating in accordance with exemplary embodiments of the present invention.

FIG. 22 shows an asset 2203(*a.*) at a location, equipped with an RFID sensor/tag and in communication with a smartphone 2201 operating in accordance with exemplary embodiments of the present invention. The asset of FIG. 22 might be, for example, located in a museum, art gallery, show room, corporate or government building, historical site, architectural structure, bridge, tower, monument, gravesite, ocean geography, recreational park and/or other geographic/campus location whether indoors or outdoors. Asset 2203 (*a.*) represents an exemplary painting referred to in the current invention as an asset. The exemplary asset is displayed to the public in a museum or any other location. The current invention includes a Smart Location Platform 2201 which could be defined as asset information database and server which could dynamically receive and transmit information regarding asset 2203 (*a.*) or other assets when in proximity or upon demand by the smartphone reader user, such as described above. The Smart location Platform 2201 might include a wireland or wireless sensor device which monitors the asset as herein described. In addition, as understood by those skilled in the art, integrated voice, IVR, SMS, SMS aggregation could be carrier independent (GSM, CDMA, IDENT) and network independent (IP, radio, UDP). In addition Smart location Platform 2201 could interface one or more deliverable nodes and modules, a secure mash-up using IDE and a secure database information archive server when accessing asset information.

In yet another embodiment of the present invention, flexible message delivery and content type could utilize push and or pull technologies. The RFID tag chip and programmed software shown as RFID sensor 2204 could contain any type of environmental sensor as well as previously described herein. The RFID tag could be equipped with a distance proximity algorithm 2206, the programmed distance 2205 from the asset could vary and be adjusted by the owner of the asset on display. Distance 2205, in this example, could be established as a security set-point by museum administration. If the security line is crossed by a person or object (e.g., a security guard) guard alert 2204 (*a.*) might notify security personnel in real-time of the situation, which in this case presents immediate danger the asset.

Another embodiment of the current invention, using the same example of a museum asset which is on display to the public, alert 2204 (*a.*) allows smartphone 2201 (by action of its user) to trigger a notification based on their "in the field" observation. Signal 604 (*b.*) from smartphone 2201 triggers a notification to a guard, an emergency responder, or other authority relative to the degree of potential harm to, or theft of, the asset. In addition, a user of smartphone 2201 might initiate an encapsulation of asset 2203 (*a.*) by activating button 2204 (*c.*). The encapsulation of the situation might be by activating the video, facial recognition, photos, audio and other technologies which could capture information regarding a situation which could endanger the asset.

Smartphone 2201 is capable of dynamically accessing information regarding asset 2203 (*a.*) display information, and an asset information archive might be accessed through the smartphone, instead of the current method of handing out phone devices or headsets (e.g., station information 2207 and video/audio/multimedia and track information 2208, 2209). The smartphone could detect which asset, station or asset through the RFID tag proximity reading application, the station or what area of the museum or campus, relative to an exhibit or selected patron interest in a certain asset such as $16^{th}$ century art or Chinese Ming Dynasty sculpture for example. The museum patron in this case could customize Italian Renaissance paintings query through the Mobile Asset Management system and Smart Location Platform. A GPS-based guiding system and map helps guide the patron to one asset to another as shown and exemplified by title 2210, history 2211; related historical archive (e.g., other similar artists) 2212; other exhibits 2213 at the site or other geographies; special features 2214 (such as for example interviews, documentaries, books, and news articles, Internet and other data access), artist archive 2215 (e.g., other paintings by the artists and where the paintings etc.), and other historical data 2216.

The smartphone reading application might, in other embodiments, provide detail of the asset when in proximity of the asset. Asset information could be in any form of text, video, audio, pictures and or multimedia regarding the painting for example or its historical linage and heritage. In addition, solar powered RFID sensors and other technologies could be used-to powered units in order to extend battery life while in transit over long distances.

GPS data pullers, also known as GPS transponders, could also be incorporated to track the asset's position at regular intervals; these devices are always-on and can be queried as often as required. GPS data pullers might be used in the case where the location of the tracker will only need to be known occasionally e.g. placed in area with high risk of a theft alert, or that does not have constant supply of power available, therefore limiting the ability to send data on a constant basis.

As described herein, some embodiments of the present invention might be implemented as a software application downloadable to a mobile device. The downloaded software application might work with existing hardware of the mobile device to implement an emergency notification alert system as described herein. For example, some embodiments might be available as an "app" or icon on the screen of the mobile device. Alternatively, some embodiments of the present invention might require special purpose hardware, and this might only be compatible with mobile devices having the emergency notification hardware.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

While the exemplary embodiments of the present invention have been described with respect to processing blocks in a software program, including possible implementation as a digital signal processor, micro-controller, or general purpose computer, the present invention is not so limited. As would be apparent to one skilled in the art, various functions of software may also be implemented as processes of circuits. Such circuits may be employed in, for example, a single integrated circuit, a multi-chip module, a single card, or a multi-card circuit pack.

The present invention can be embodied in the form of methods and apparatuses for practicing those methods. The present invention can also be embodied in the form of program code embodied in tangible media, such as magnetic recording media, optical recording media, solid state memory, floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits. The present invention can also be embodied in the form of a bitstream or other sequence of signal values electrically or optically transmitted through a medium, stored magnetic-field variations in a magnetic recording medium, etc., generated using a method and/or an apparatus of the present invention.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements. Signals and corresponding nodes or ports may be referred to by the same name and are interchangeable for purposes here.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A personal safety notification system comprising:
   a plurality of mobile devices in wireless communication with a network;
   a server, coupled to the network, configured to communicate with each mobile device, wherein the server is coupled to a database comprising personal safety information related to predefined alerts/events, and is coupled to one or more other databases including one or more of geographic, topological, building, structure and area configuration information; and
   a plurality of nodes configured to provide a perimeter about an area and coupled to the server wherein, when one or more of the plurality of mobile devices enters the area, the corresponding mobile device enters an active sub-network within the personal safety notification system coordinated by the server,
   wherein the server is further configured to receive alert/event details from each mobile device in the active sub-network, and provide the alert/event details to specific ones of the plurality of mobile devices in the active sub-network in response to the occurrence of a given alert/event, the alert/event details including X-Y-Z coordinate information for aspects of the area within the active sub-network.

2. The personal safety notification system of claim 1, wherein, when the given alert/event occurs within the area comprising the active sub-network:
for selected ones of the plurality of mobile devices, the server is configured to provide i) information of the corresponding given alert/event, and ii) associated information related to corresponding geographic, topological, building, structure and area configuration information related to the given alert/event, wherein the associated information includes the X-Y-Z coordinate information within the active sub-network.

3. The personal safety notification system of claim 2, wherein the associated information includes a map overlay and classified safe and hazardous routes in relation to the specific alert/event.

4. The personal safety notification system of claim 2, wherein one or more of the plurality of mobile devices in the active sub-network are configured to capture, timestamp and display aspects of a given alert/event when experienced by the corresponding user.

5. The personal safety notification system of claim 2, wherein each mobile device is at least one of a wireless phone, smartphone, lockbox, laptop computer, notebook, WiFi enabled device, a wireless triggering device, and a radio.

6. The personal safety notification system of claim 5, wherein the mobile device is enabled with a security process selected from a password key, cryptographic function key, and biometric key.

7. The personal safety notification system of claim 5, wherein the mobile device includes a Global Positioning System (GPS) module configured to collect GPS location information related to the mobile device for the given alert/event.

8. The personal safety notification system of claim 5, wherein the mobile device includes a display, wherein the mobile device, in coordination with the server, is configured to classify information related to the mobile device for the given alert/event and provide such classified information via the display.

9. The personal safety notification system of claim 2, wherein, within the perimeter, the personal safety notification system further comprises coordinate devices associated with predetermined geographic, topological, building, structure and area configuration aspects of the area configured to provide corresponding X-Y-Z coordinate information, wherein each coordinate device is configured to match with a corresponding mobile device specific X-Y-Z coordinate information of at least one of geographic, topological, building, structure and area configuration aspects of the area related to the given alert/event when reported from the corresponding mobile device.

10. A mobile device coupled to a server providing database information related to a personal safety notification system, comprising:
a sensor configured to read alert/event data in proximity to the mobile device;
a processor configured to control collection of the alert/event data by the sensor of the mobile device, the alert/event data having associated X-Y-Z coordinate information of the mobile device and each alert/event;
a memory configured to store the alert/event data collected by the mobile device,
a wireless transceiver, in wireless communication with the server, configured to transfer the alert/event data collected by the mobile device to the server,
wherein, when the mobile device enters an area defined by a plurality of nodes configured to provide a perimeter about the area and coupled to the server, the mobile device enters an active sub-network within a personal safety notification system coordinated by the server through communication with the processor through the wireless transceiver.

11. The mobile device of claim 10, wherein the sensor is at least one of a camera, a microphone, an infrared detector and a radio detector.

12. The mobile device of claim 11, wherein the mobile device further comprises a Global Positioning System (GPS) module configured to generate the associated X-Y-Z coordinate information of the mobile device and each alert/event.

13. The mobile device of claim 12, wherein the mobile device is further configured to communicate with coordinate devices associated with predetermined geographic, topological, building, structure and area configuration aspects of the area configured to provide corresponding X-Y-Z coordinate information, wherein each coordinate device is configured to match with a corresponding mobile device specific X-Y-Z coordinate information of at least one of geographic, topological, building, structure and area configuration aspects of the area related to the given alert/event when reported from the corresponding mobile device in coordination with the GPS module of the mobile device.

14. The mobile device of claim 10, wherein, when a given alert/event occurs within the area comprising the active sub-network:
for selected ones of the plurality of mobile devices, the mobile device is configured to provide to the server i) information of the corresponding given alert/event, and ii) associated information related to corresponding geographic, topological, building, structure and area configuration information related to the given alert/event, wherein the associated information includes the X-Y-Z coordinate information within the active sub-network.

15. The mobile device of claim 10, wherein each mobile device is at least one of a wireless phone, smartphone, lockbox, laptop computer, notebook, WiFi enabled device, a wireless triggering device, and a radio.

16. The mobile device of claim 15, wherein the mobile device is enabled with a security process selected from a password key, cryptographic function key, and biometric key.

17. The mobile device of claim 15, wherein the mobile device is a lockbox in wireless communication with the server, the lockbox further configured to detect an emergency situation and report the emergency situation to the server.

18. The mobile device of claim 15, wherein the mobile device includes a display, wherein the mobile device, in coordination with the server, is configured to classify information related to the mobile device for the given alert/event and provide the classified information via the display.

19. The mobile device of claim 15, wherein the mobile device includes a display, wherein the mobile device, in coordination with the server, is configured to overlay X-Y-Z coordinate information related to a location of the mobile device with a map on the display.

20. A method for alerting campus members of a campus emergency by a personal safety notification system, comprising:
communicating, by a server, with a plurality of mobile devices in wireless communication via a network;

collecting, by the server, alert/event details from one or more of the plurality of mobile devices, wherein the server is coupled to a database comprising personal safety information related to predefined alerts/events, and is coupled to one or more other databases including one or more of geographic, topological, building, structure and area configuration information; and establishing, by a plurality of nodes, a perimeter about the campus and coupled to the server wherein, when one or more of the plurality of mobile devices enters the area, the corresponding mobile device enters an active sub-network within the personal safety notification system coordinated by the server, providing, by the server, at least a portion of the alert/event details to specific ones of the mobile devices in the active sub-network in response to the occurrence of a given alert/event, the alert/event details including X-Y-Z coordinate information for aspects of the area within the active sub-network based on the one or more of geographic, topological, building, structure and area configuration information specific to the campus.

* * * * *